US012521508B2

(12) United States Patent
Gulka et al.

(10) Patent No.: US 12,521,508 B2
(45) Date of Patent: Jan. 13, 2026

(54) RESPIRATORY INTERFACE

(71) Applicant: Trudell Medical International Inc., London (CA)

(72) Inventors: Noel Gulka, London (CA); George Baran, London (CA)

(73) Assignee: Trudell Medical International Inc., London (CA)

(*) Notice: Subject to any disclaimer, the term of this patent is extended or adjusted under 35 U.S.C. 154(b) by 961 days.

(21) Appl. No.: 17/143,811

(22) Filed: Jan. 7, 2021

(65) Prior Publication Data

US 2021/0236758 A1 Aug. 5, 2021

Related U.S. Application Data

(63) Continuation of application No. 14/994,732, filed on Jan. 13, 2016, now Pat. No. 10,912,908.

(Continued)

(51) Int. Cl.

*A61M 16/04* (2006.01)
*A61M 15/00* (2006.01)
*A61M 16/20* (2006.01)

(52) U.S. Cl.

CPC ...... *A61M 16/0488* (2013.01); *A61M 15/009* (2013.01); *A61M 16/208* (2013.01); *A61M 2210/065* (2013.01)

(58) Field of Classification Search

CPC .......... A61J 7/00; A61J 7/0015; A61J 7/0046; A61J 7/0053; A61J 7/0076; A61J 17/001;

(Continued)

(56) References Cited

U.S. PATENT DOCUMENTS 5,042,467 A 8/1991 Foley
5,685,291 A * 11/1997 Marsh .............. A61M 16/0495 128/200.15

(Continued)

FOREIGN PATENT DOCUMENTS

CN 10181552 8/2010
CN 103007408 A 4/2013

(Continued)

OTHER PUBLICATIONS

International Search Report and Written Opinion for International Application No. PCT/IBZ016/050143 mailed on Apr. 13, 2016.

(Continued)

*Primary Examiner* — Elliot S Ruddie
(74) *Attorney, Agent, or Firm* — Crowell & Moring LLP

(57) ABSTRACT

A patient respiratory interface for use in an aerosol delivery system is disclosed. The interface may provide a mechanism for introducing an aerosolized medicament to infants without the need for invasive intubation when treating issues in infants such as infant respiratory distress syndrome. The interface may include an outer body formed in the shape of a pacifier where the insertion portion of the pacifier may be hollow and have an opening to guide a catheter or other tubing that may be passed through a flange and the insertion portion of the interface. The catheter may be recessed from or extend slightly out of the tip of the insertion portion so that a flow of nebulized medicament may be delivered to the patient's oropharynx in aerosol form.

17 Claims, 33 Drawing Sheets

Related U.S. Application Data

(60) Provisional application No. 62/102,813, filed on Jan. 13, 2015.

(58) Field of Classification Search

CPC ........ A61J 17/006; A61J 17/008; A61J 11/00; A61J 11/0005; A61J 11/001-002; A61J 11/02; A61M 16/0486; A61M 16/0488; A61M 15/0021; A61M 15/0016; A61M 15/0018; A61M 16/049; A61M 16/0493; A61M 16/0495; A61M 16/0497; A61M 11/02; A61M 15/0086; A61M 15/0088; A61M 15/009; A61M 16/20; A61M 16/208; A61M 16/209; A61M 11/06; A61M 16/0816; A61M 2240/00; A61M 13/00

USPC ................ 128/207.14, 207.15; 606/234, 236

See application file for complete search history.

(56) References Cited

U.S. PATENT DOCUMENTS

| | | | | |
|---|---|---|---|---|
| 5,823,179 | A | 10/1998 | Grychowski et al. | |
| 5,964,223 | A | 10/1999 | Baran | |
| 6,139,566 | A | 10/2000 | Bennett | |
| 6,293,279 | B1 | 9/2001 | Schmidt et al. | |
| 6,526,976 | B1 * | 3/2003 | Baran | A61M 16/042 128/207.14 |
| 6,557,548 | B1 | 5/2003 | Dickson | |
| 6,626,168 | B1 | 9/2003 | Carroll et al. | |
| 6,776,157 | B2 | 8/2004 | Williams et al. | |
| 6,929,003 | B2 | 8/2005 | Blacker et al. | |
| 7,318,433 | B2 | 1/2008 | Cockerham | |
| 2003/0029447 | A1 * | 2/2003 | Vito | A61M 15/009 128/200.23 |
| 2004/0094148 | A1 * | 5/2004 | Lulla | A61M 15/0086 128/200.23 |
| 2007/0039614 | A1 | 2/2007 | Djupesland | |
| 2008/0000470 | A1 | 1/2008 | Minocchieri et al. | |
| 2008/0196716 | A1 * | 8/2008 | Wachter | A61M 15/002 128/203.12 |
| 2010/0140204 | A1 * | 6/2010 | Vischer | A61J 11/0075 215/11.1 |
| 2010/0313886 | A1 | 12/2010 | Wachtel et al. | |
| 2011/0240015 | A1 | 10/2011 | Nikander et al. | |
| 2012/0048264 | A1 | 3/2012 | Finlay et al. | |
| 2013/0245576 | A1 | 9/2013 | Hoogenakker et al. | |
| 2013/0333695 | A1 | 12/2013 | Dellaca et al. | |
| 2014/0116436 | A1 | 5/2014 | Bruce et al. | |
| 2014/0216449 | A1 | 8/2014 | Chang | |
| 2014/0311483 | A1 | 10/2014 | Engelbreth et al. | |
| 2017/0368276 | A1 | 12/2017 | Egan | |

FOREIGN PATENT DOCUMENTS

| | | | | |
|---|---|---|---|---|
| CN | 203227180 U | | 10/2013 | |
| CN | 203861709 U | | 10/2014 | |
| GB | 2327223 A | * | 1/1999 | A61J 17/00 |
| JP | 1996-38607 | | 2/1996 | |
| JP | 2007-501087 | | 1/2007 | |
| JP | 2013-188479 | | 9/2013 | |

OTHER PUBLICATIONS

Japanese Office Action for corresponding application No. 2017-537221, including translation, dated Oct. 17, 2019.

Search Report for Chinese Patent Application No. 2016800101936 dated Dec. 18, 2019 (3 pages).

Japanese Office Action including translation for Patent Application No. 2017-537221 dated Jul. 6, 2020 (6 pages).

* cited by examiner

RESPIRATORY INTERFACE

CROSS-REFERENCE TO RELATED APPLICATIONS

This application is a continuation of U.S. application Ser. No. 14/994,732, filed Jan. 13, 2016, issued Feb. 9, 2021 as U.S. Pat. No. 10,912,908, which claims the benefit of U.S. Provisional Patent App. No. 62/102,813, filed Jan. 13, 2015, wherein the entirety of each of these prior applications is hereby incorporated herein by reference.

TECHNICAL FIELD

This disclosure relates to a respiratory interface. More particularly, this disclosure relates to a respiratory interface for use in delivering an aerosolized substance to an infant, child or adult.

BACKGROUND

Infant respiratory distressed syndrome may be caused by a lack of pulmonary surfactant. The current practice for the treatment of surfactant deficient infants is to instill a liquid surfactant suspension. Typical surfactant installation therapy requires endotracheal intubation. As might be expected with infants, there can be several difficulties with such surfactant installation therapy. These problems may include the fact that the endotracheal intubation is intrusive and has potential side effects for the infant. Installation of a liquid surfactant may provide an uneven distribution within the infant's lung. Additionally, installation of a liquid may temporarily block ventilation for the infant.

BRIEF SUMMARY

A patient respiratory interface for use in an aerosol delivery system is disclosed. The interface may provide a mechanism for introducing an aerosolized medicament or liquid to a patient, such as an adult, child or infant without the need for invasive intubation, such as, for example, when treating respiratory distress syndrome in infants. The interface may include an outer body formed in the shape of a pacifier where the insertion portion of the pacifier may be hollow and have an opening to guide a catheter or other tubing that may be passed through a flange and the insertion portion of the interface. The catheter may be recessed from or extend slightly out of the tip of the insertion portion so that a flow of nebulized medicament may be delivered to the patient's oropharynx in aerosol form or partially in aerosol form.

In one aspect a patient respiratory interface may include an insertion portion sized to only extend partially within an oral cavity of a patient. A flange attached to, and having a surface oriented substantially perpendicular to, the insertion portion may serve to limit the distance that the insertion portion may extend into the patient's oral cavity. A supply pathway or nebulization supply pathway is defined by the insertion portion and the flange. The supply pathway or nebulization supply pathway may be positioned coaxially along a longitudinal axis of the insertion portion and sized to receive at least one lumen carrying a supply of a pressurized gas and a substance. The substance may consist of, without limitation, of a medicament in liquid form or other therapeutic substance in liquid or dry powder form. The insertion portion and flange are arranged in a shape to permit introduction of an aerosolized substance or partially aerosolized substance to an oropharynx of the patient through a center of the insertion portion. One suitable shape, without limitation, is a shape approximating the shape of a pacifier or soother.

DETAILED DESCRIPTION

Figure 1:
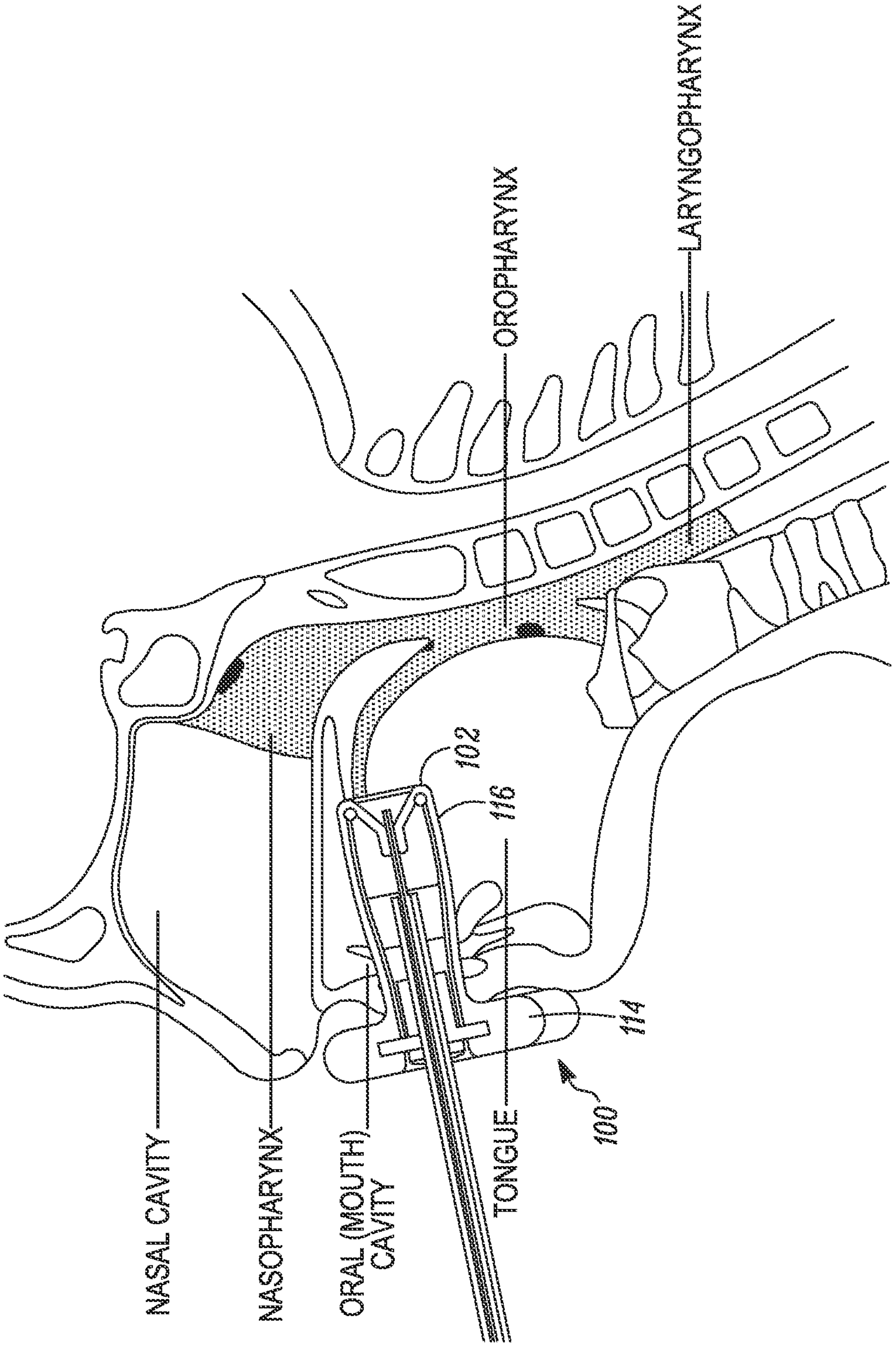
FIG. 1 illustrates a patient respiratory interface in the form of a pacifier according to one embodiment in relation to an anatomical cross-section of an upper respiratory system.

Referring to FIG. 1, a cross-section of a hypothetical patient head area is illustrated showing an embodiment of a patient respiratory interface 100 to a respiratory system of the patient. The patient respiratory interface 100 (also referred to herein as the neonatal interface or interface) is shown as taking the form of a pacifier commonly used to calm an infant or child. The patient interface 100, as described in greater detail below, is configured with a passageway that allows tubing with one or more lumens, for example a catheter, to pass completely through the body of the interface and align with the center of the tip of the pacifier body or other body form of the interface such that a gas or an aerosolized substance, or partially aerosolized substance, may be introduced into the oropharynx area of the patient's airway from approximately the center of the patient's mouth. In embodiments where the interface 100 is in the form of a pacifier, the distal end of the interface may only reach a limited distance such that the tip 102 of the interface 100 does not extend past the oral cavity to cause any patient discomfort, but that allows the aerosol to reach the oropharynx so that it may be inhaled to coat the lungs. The interface is sized to protect the tip of the tubing and position the tip of the tubing as close to the patient's airway as possible without being overly invasive.

Figure 2:
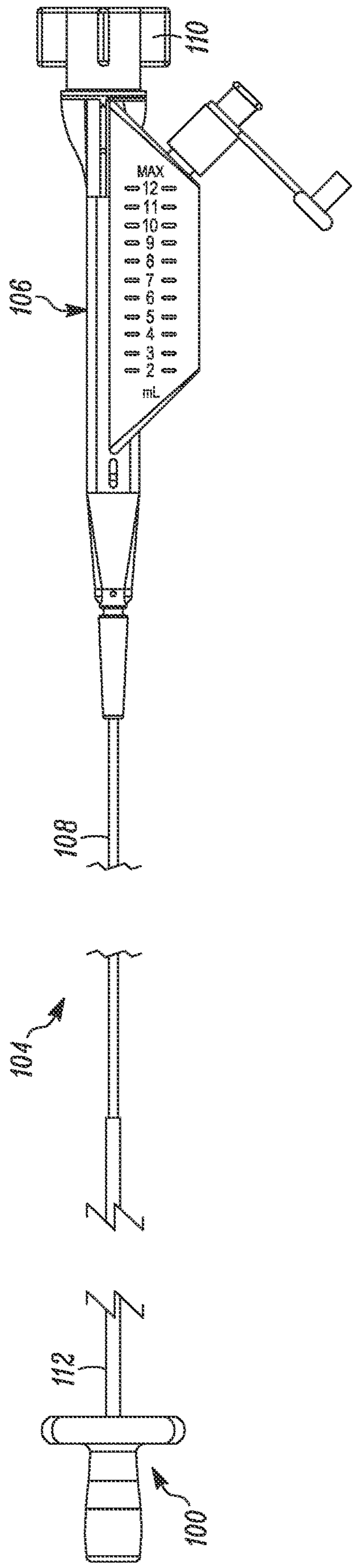
FIG. 2 illustrates one example aerosol delivery system incorporating the patient respiratory interface of FIG. 1.

Referring to FIG. 2, an aerosol delivery system 104 that includes the patient respiratory interface 100 is illustrated. The aerosol delivery system may include a liquid vessel and multi-lumen tubing (106, 108). The liquid vessel 106 may hold a self-contained refillable supply of a liquid to be nebulized and the multi-lumen tubing 108 may carry a gas with a gas supply attached to the end of the aerosol delivery system. A resealable fitting 110 for connecting with a gas supply may be positioned on one end of the aerosol delivery system adjacent the liquid vessel 106. The vessel 106 may include a body having a liquid reservoir and a gas passage independent of the liquid reservoir, where the liquid reservoir and gas passage are in communication with the gas supply via the resealable fitting 110. The vessel 106 is configured to be positioned adjacent the gas supply when the resealable fitting 110 is attached to the gas supply. A second end of the vessel 106 is connected with the multi-lumen tubing 108. The second end may define a liquid path from the liquid reservoir within the vessel 106 to a liquid lumen in the multi-lumen tubing 108, as well as a gas path from the gas passage within the vessel 106 to at least one gas lumen in the multi-lumen tubing 108. One suitable aerosol delivery system for use with the interface 100 is illustrated in U.S. Patent Pub. No. 2012/0048264 A1, the entirety of which is hereby incorporated by reference herein.

In one embodiment, the multi-lumen tubing 108 carries the liquid and gas along its length to the patient respiratory interface 100. The length of the multi-lumen tubing 108 may be selected as necessary to provide the appropriate distance between the interface 100 and the vessel 106 of the aerosol delivery system 104. In one embodiment, it is contemplated that the tubing have at least one liquid lumen and at least one gas lumen, for example a plurality of gas lumens surrounding a central liquid lumen. Additionally, the orifices at the distal end of the tubing 108 may be configured to cause the gas and liquid to mix into an aerosol as the gas and liquid exit the tubing. In another implementation, the tubing may include multiple lumens within a portion of its length and then an internal mixing area where the gas and liquid are mixed prior to exiting the tubing. In yet another embodiment, the tubing may have only a single lumen that carries both the gas and the liquid. A strain relief portion 112 may be affixed to one end of the interface 100 to minimize pinching or excessive force being concentrated at the end of the multi-lumen tubing 108 where the tubing meets the interface 100. Using the aerosol delivery system and interface, it is contemplated that a continuously produced aerosol may be produced having a particle size in the range of 10-14 micrometers mass median aerodynamic diameter (MMAD) when gas at a pressure of 50 pounds per square inch (p.s.i.) is received at the resealable fitting 110.

Figure 3B:
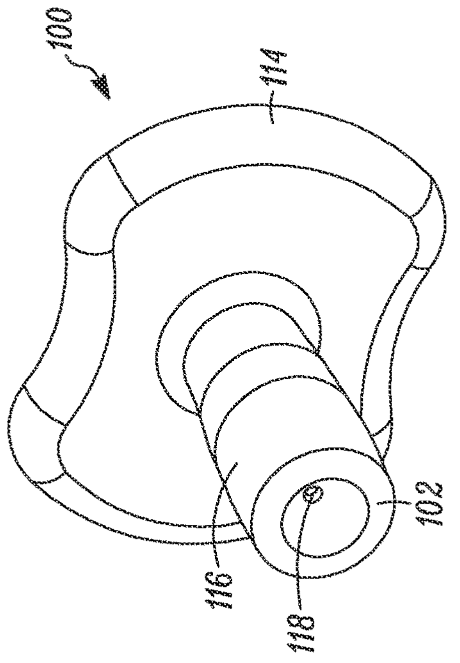
FIGS. 3A-3D show top (3A), perspective (38), front (3C) and side (3D) views of the patient respiratory interface of FIG. 1
Figure 3C:
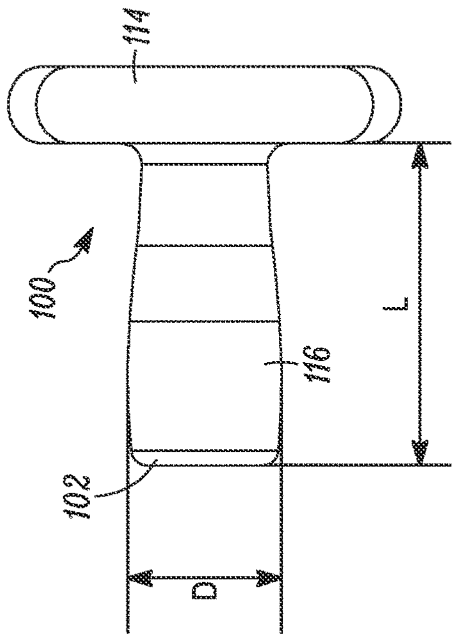
Figure 3A:
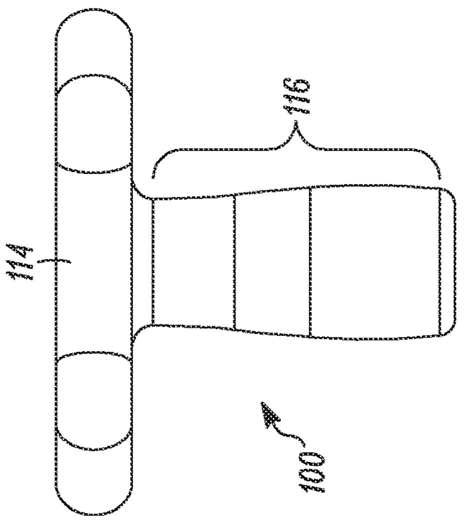
Figure 3D:
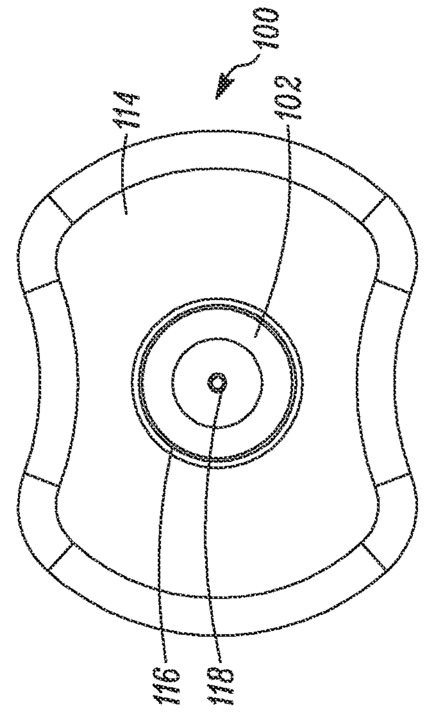

FIGS. 3A-3D illustrate different views of an embodiment of the interface 100. The interface 100 may include a flange portion 114 and an insertion portion 116. The insertion portion 116 is intended for insertion into the mouth of the infant with the flange 114 providing a stop member to limit the distance within which the insertion member 116 may penetrate into an oral cavity. The insertion and flange portions 116, 114 may be made of the same material or different materials. It is contemplated that the insertion portion 116 be constructed of a flexible material such as is used in standard pacifiers, for example silicone, that is safe for oral contact. A chamber-like region is defined by the inside of the insertion portion. As best shown in FIGS. 3B and 3D, the insertion portion 116 may include a coaxially aligned opening 118 through the center of the insertion portion that is located in a recessed region adjacent the tip 102 of the interface 100. The dimensions of the insertion portion may vary depending on the size and age of the intended patient. In one embodiment for use with an infant, the maximum diameter range D and length range L (FIG. 3C) may be 10-20 millimeters (mm) and 15-35 mm, respectively.

Figure 4B:
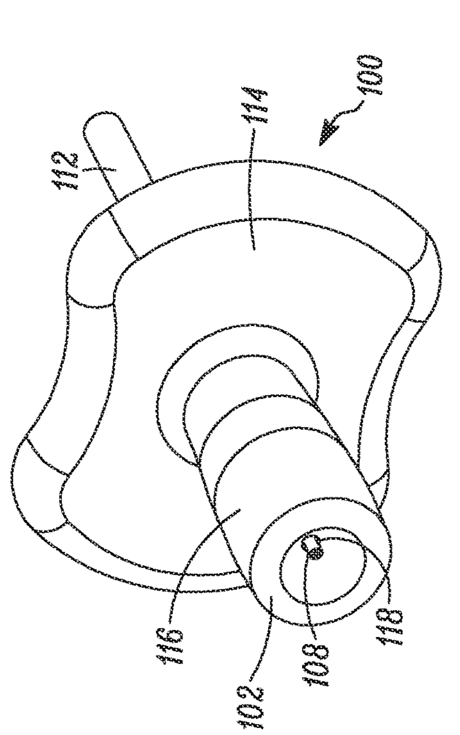
FIG. 4A-4D show top (4A), perspective (48), front (4C) and side (4D) views of the patient respiratory interface of FIG. 1 including a strain relief sleeve and multi-lumen tubing.
Figure 4C:
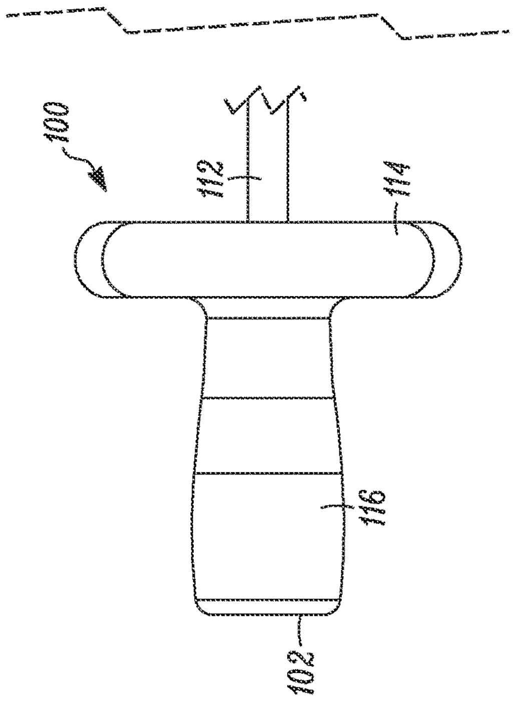
Figure 4A:
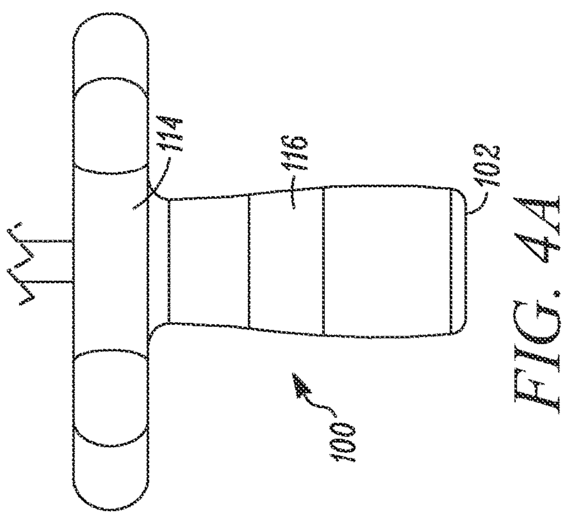
Figure 4D:
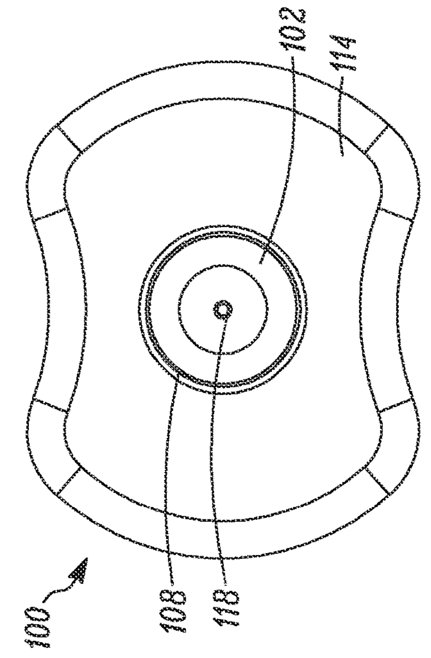

Referring to FIGS. 4A-4D, the interface of FIGS. 3A-3D is shown with a strain relief sleeve 112 extending from the flange 114 opposite the side of the flange from the insertion portion 116. The strain relief sleeve may extend from within the insertion portion of the interface through the flange 114 and may extend away from the other side of the flange 114 a short distance to protect the multi-lumen tubing 108. FIGS. 4B and 4D illustrate the multi-lumen tubing 108 extending through the opening 118 near the tip 102 of the interface 100 after it extends beyond the strain relief sleeve inside the insertion portion.

Figure 5:
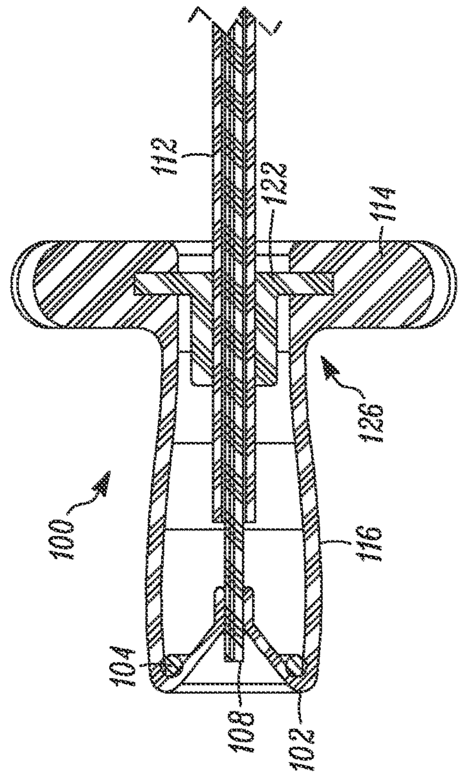
FIG. 5 is a cross-sectional view of the patient respiratory interface of FIG. 4C.
Figure 6:
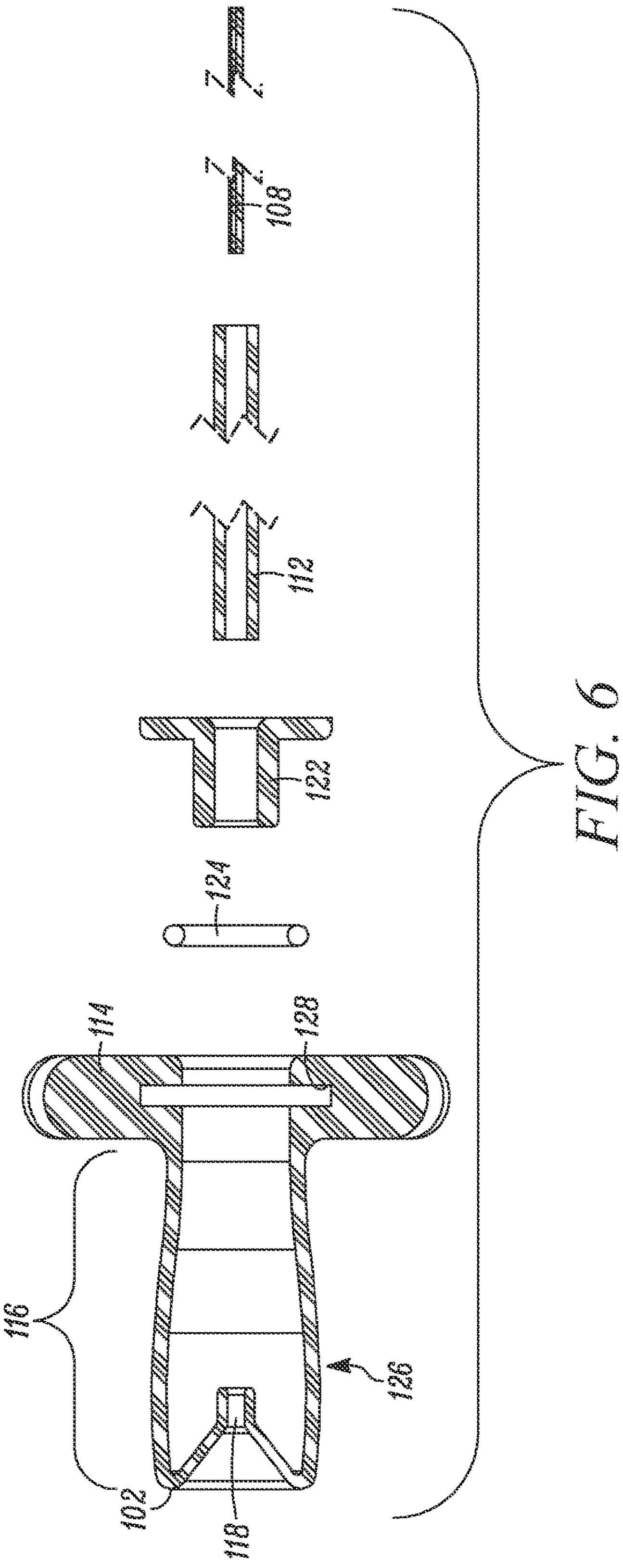
FIG. 6 is an exploded side view of the patient respiratory interface of FIG. 5

Referring now to FIG. 5, a cross-sectional view of the interface 100 of FIGS. 2-4 is shown with the multi-lumen tubing 108 fully inserted through the strain relief sleeve 112 and passing through the opening 118 in the insertion member 116. As best seen in FIG. 6, the interface 100 may be made up of several components. The outer component or body 126 of the interface being the pacifier portion made of a flexible material such as silicone. The insertion portion 116 is hollow with an opening 118 positioned at a region folded back and recessed from the tip 102. The tip 102 may be supported with a support ring 124 positioned on the inside of the tip 102 of the body 126 to assist with maintaining the shape of the insertion portion 116. The body 126 may curve out from an initial diameter at the point where it meets with the flange to a slightly wider diameter at the tip 102. Fastener and guide piece 122 may form a friction fit in a slot 128 formed within the body 126. The fastener and guide 122 is sized with flanges to fit into the slots 128 and has a hollow central axis sized to accept a strain relief sleeve 112 in a friction fit or other fastening technique. The multi-lumen tubing 108 is sized to fit through the hollow shaft of the strain relief sleeve 112 and may either be fixedly attached to the strain relief sleeve 112 or removably attached to the strain relief sleeve 112, such as slidably attached in a friction fit.

In one embodiment it is contemplated that the multi-lumen tubing or catheter 108 may be made of a nylon material or any of another number of flexible materials suitable for use with gases, liquids, and/or dry powders and maintaining one or more lumens within its interior. The strain relief sleeve 112 may be made of a rigid material such as PVC (polyvinylchloride). The fastener and guide insert 122, as well the support ring 124 may each be made of a more rigid material such as a thermoplastic resin. The fastener and guide 122 and support ring 124 each provide rigidity and/or shape to the outer body 126 of the pacifier type interface 100. In the embodiment of FIGS. 2-6, the interface 100 is sized to guide a single, coaxially positioned length of multi-lumen tubing, such as a catheter. The multi-lumen tubing 108 may be positioned to be slightly recessed within the tip 102 of the hollow body 126 of the interface 100, or may be visibly positioned to extend slightly beyond the tip 102.

Figure 7A:
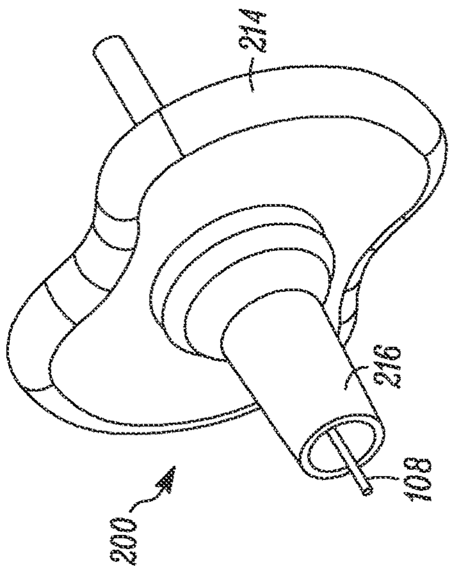
FIGS. 7A-7D illustrate front perspective (7A), rear perspective (78), rear (7C) and side (7D) views of a first alternative embodiment of the patient respiratory interface of FIG. 1 with a relief valve.
Figure 7B:
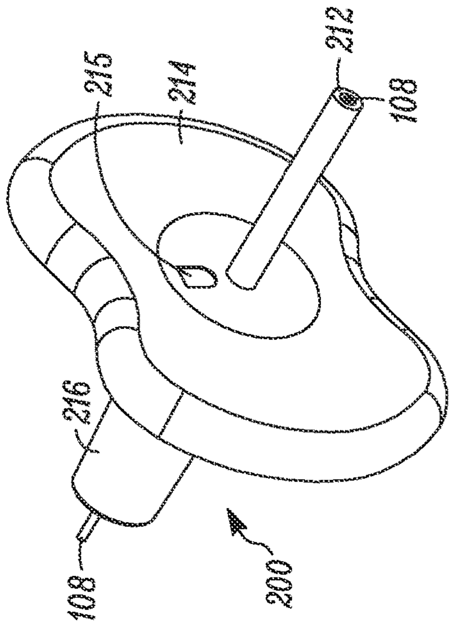
Figure 7C:
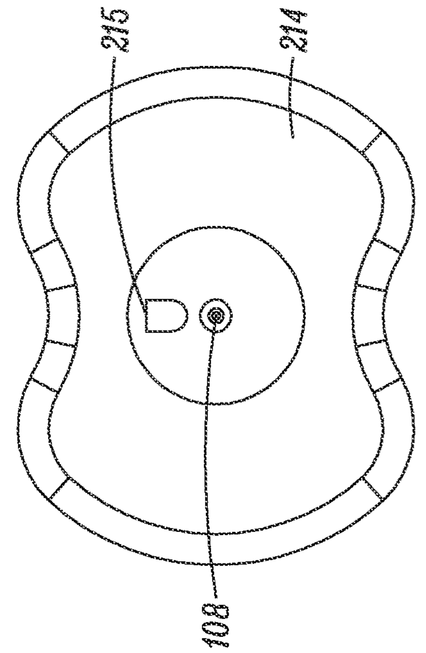
Figure 7D:
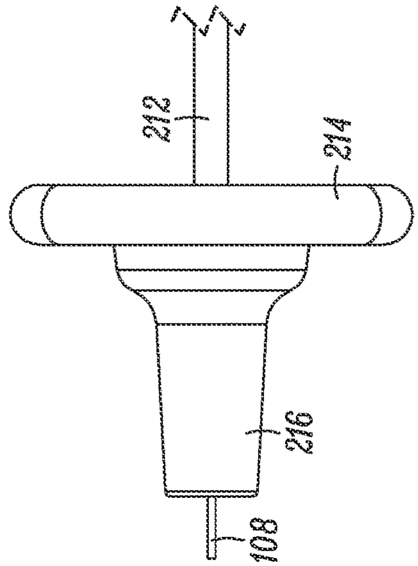
Figure 8:
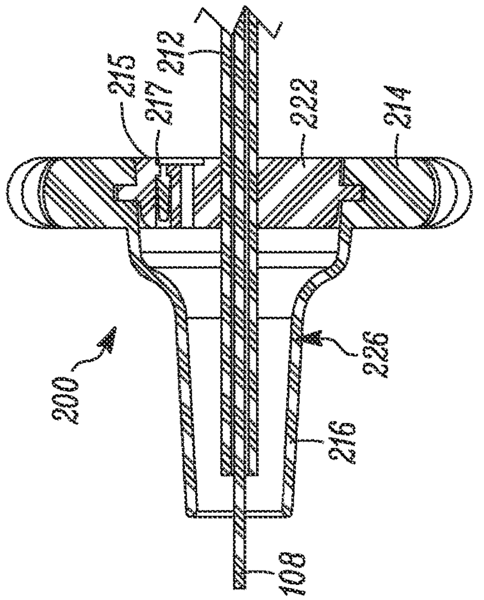
FIG. 8 is a cross-sectional view of the patient respiratory interface of FIG. 7D
Figure 9:
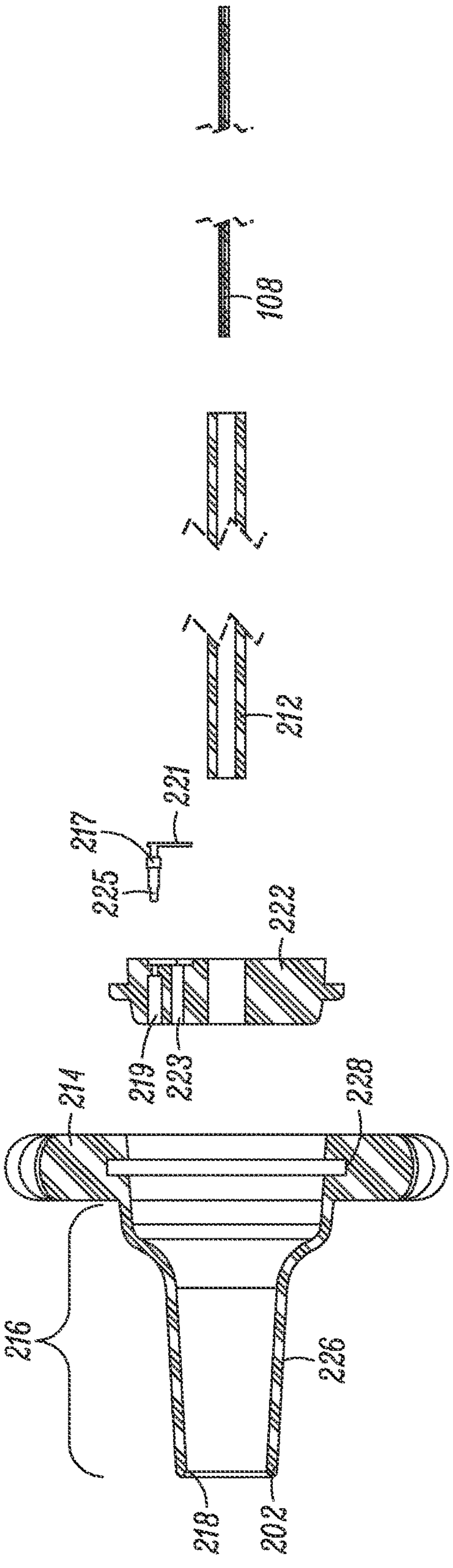
FIG. 9 is an exploded side view of the patient respiratory interface of FIG. 8
Figure 10A:
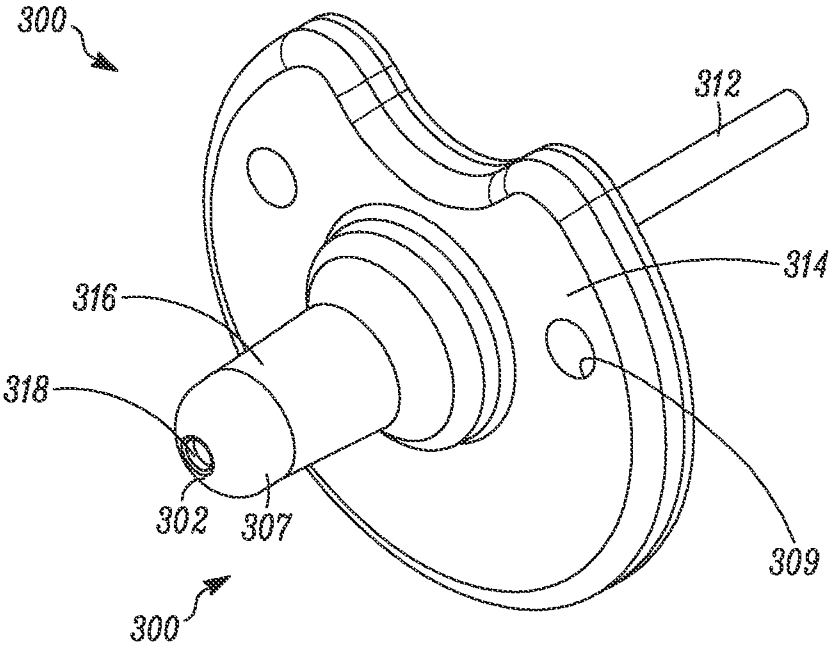
FIGS. 10A-10D illustrate front perspective (10A), top (10B), side (10C) and front (10D) views of a second alternative embodiment of the patient respiratory interface of FIG. 1.
Figure 10B:
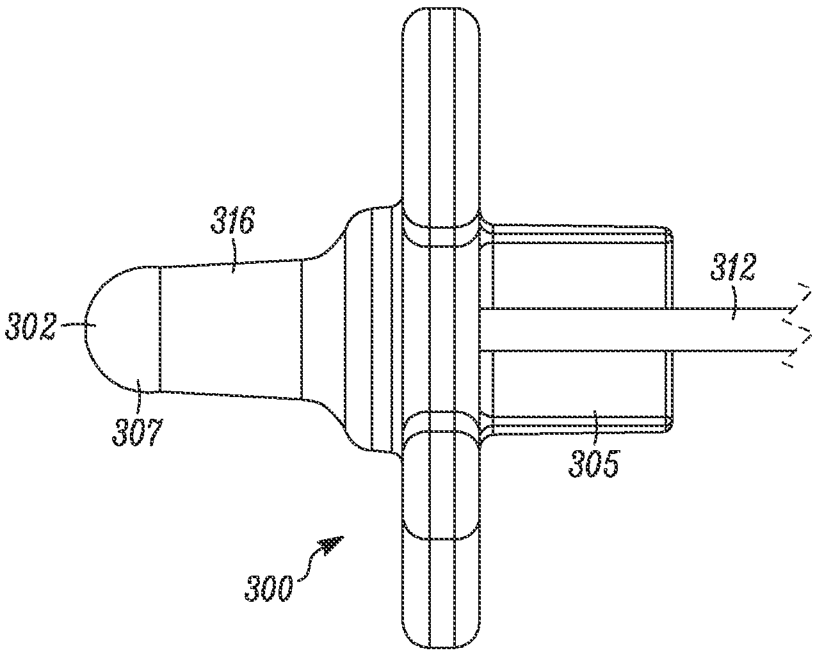
Figure 10C:
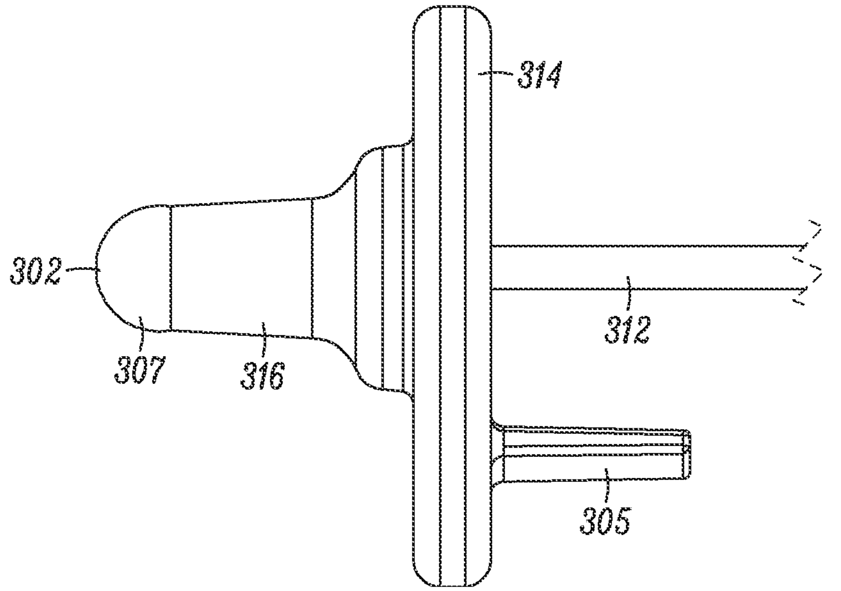
Figure 10D:
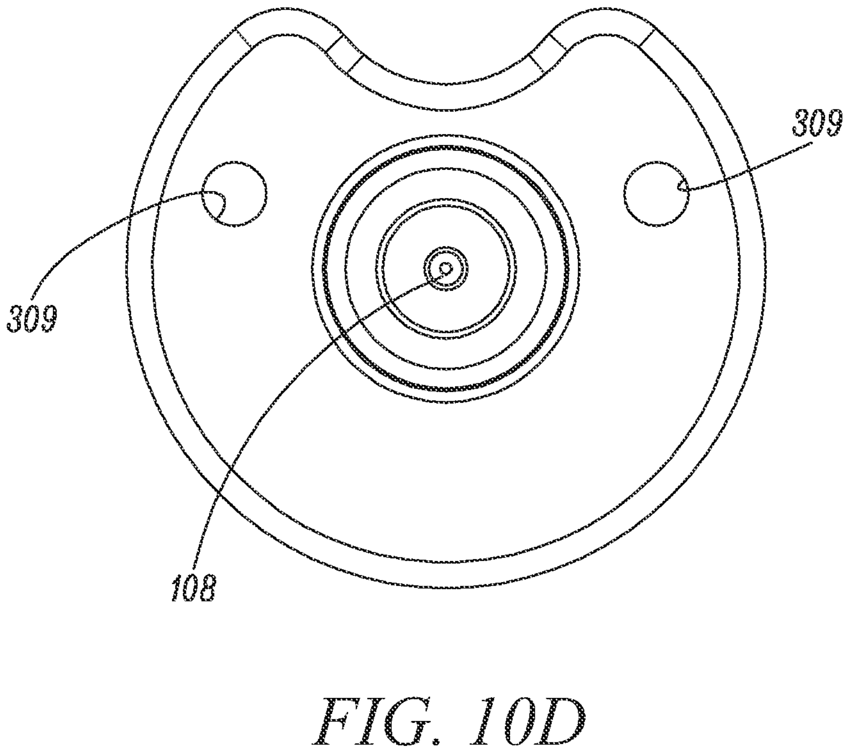
Figure 11:
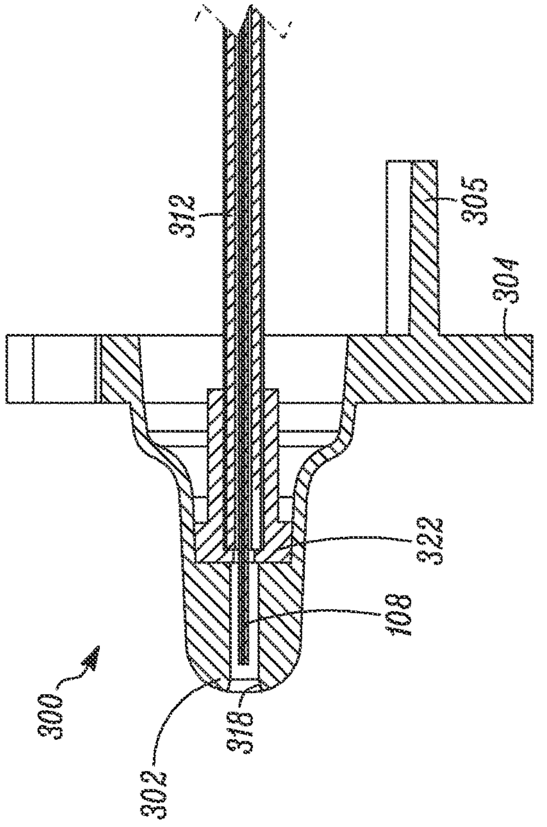
FIG. 11 is a cross-sectional view of the patient respiratory interface of FIG. 10C.

An alternative patient respiratory interface embodiment which includes a pressure relief port is illustrated in FIGS. 7A-7D, as well as FIGS. 8 and 9. The interface 200 shown in FIGS. 7-9 also includes a slightly different shaped insertion portion 216 and flange 214. The insertion portion 216 of this embodiment of the interface 200 includes a continuously tapering profile broken up into different sections or taper profiles. Positioned in the flange 214, a pressure relief assembly 215 allows excess pressure building up in the patient to pass through the insertion portion 216 and out the pressure relief assembly 215 in the flange 214. The position of the multi-lumen tubing 108 is also illustrated in FIGS. 7B and 7C where, as in the interface 100 of FIGS. 2-6, the multi-lumen tubing 108 is centrally located and should pass through the flange 214 and insertion portion 216 into the oral cavity of the patient.

FIGS. 8 and 9 illustrate the interface 200 of FIGS. 7A-7D in greater detail. In the pressure relief assembly 215, a pressure relief valve 217 fits into a fastener and guide 222 to cover a pressure relief port 223 in the fastener and guide 222. The pressure relief valve 217 includes a valve flap 221 that is moveably positioned over the pressure relief port 223 and an anchor portion 225 sized to fit in a receiving region 219 of the fastener and guide 222. The external portion of the interface 200 is formed of a single pacifier outer body 226 somewhat similar to that of the embodiment of FIGS. 2-5, but with an opening 218 at the tip 202 of the interface 200 rather than a recessed opening 118 slightly preceding the tip 102 of the interface 100 in FIGS. 2-6. The fastener and guide 222 with the relief port 223 fits into the flange portion 214 of the interface 200 in a receiving slot 228 formed annularly within the inner diameter of the pacifier body 226. The fastener and guide 222 has a central axial passageway for receiving the strain relief sleeve 212 that is sized to then receive the catheter or multi-lumen tubing 108. As shown in FIG. 8, when fully assembled and at rest, the pressure relief valve 215 is closed such that the pressure relief port 223 is covered by the flap 221. If too much pressure is received within the infant's oral cavity then the space on inner diameter of the opening 218 will pass on any extra pressure through the insertion portion 216 through the pressure relief port 223 and out the flap 221 of the pressure relief valve 217 which will open in response to an increase pressure on the insertion portion side of the flange 214 above a predetermined pressure. Also, in this embodiment the multi-lumen tubing 108 is shown extended passed the tip 202 of the insertion portion 216. It is contemplated that the pressure relief valve 217 may be made of any of a number of flexible materials, such as silicone.

Any of a number of shapes of the insertion portion and flange of the pacifier-type patient respiratory interface are contemplated. For example, FIGS. 10A-10D, and 11-12 illustrate a slightly altered shape of the interface 300 as compared with the interfaces of the embodiments of FIGS. 1-6 and 7-10. For example, the insertion portion 316 has a rounded distal end 307 that terminates at a tip 302 that defines an opening 318 flush with the tip, rather than the recessed opening 118 of the embodiment of FIGS. 1-6. Additionally, the opening 318 in FIGS. 10A-10D shows a smaller diameter than the opening 218 at the tip 202 in the embodiment of FIG. 7-9. Also, the shape of the flange 314 differs than prior flange embodiments. Openings 309 to accept a retaining strap are provided. Additionally, on the side of the flange 314 opposite the insertion portion 316 there is included a tab 305 which may act as a grip to medical professionals or the patient to insert or remove the interface 300. The catheter or multi-lumen tubing 108 is again shown as centrally located in a coaxial manner in the insertion portion 316. Opposite the insertion portion 316 and adjacent the tab 305 the strain relief sleeve 312 may extend out from the flange 314.

Figure 12:
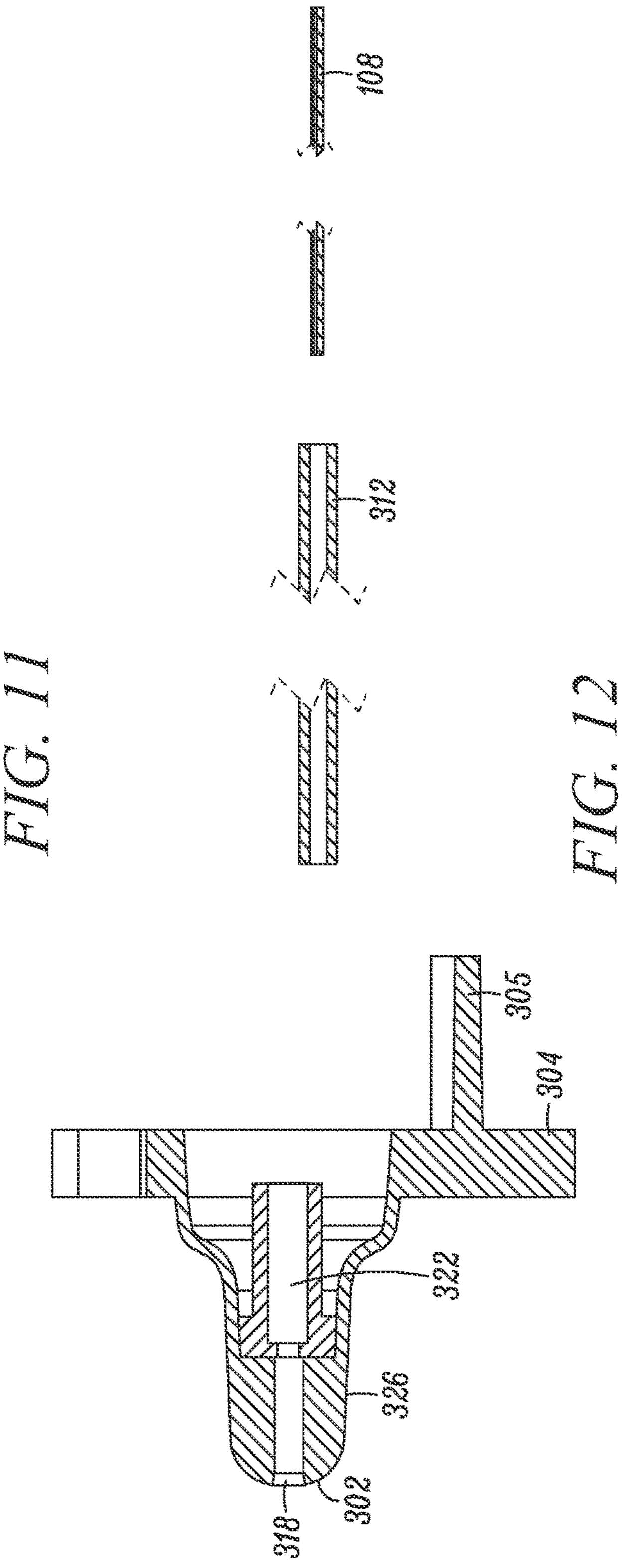
FIG. 12 is an exploded side view of the patient respiratory interface of FIG. 11.

As shown in FIG. 12, a cross-section exploded view of the embodiment of FIGS. 10A-10D is shown. In this instance, the outer body 326 of the pacifier portion of the interface 300 shows thicker walls of the insertion portion as compared to the prior embodiments, the fastener and guide 322 fits more deeply into the insertion portion 316 than in the prior embodiments. As with the prior embodiments, a central axis through the fastener and guide 322 is sized to receive a strain relief sleeve 312 in a friction fit manner, or in another adhesive or attachment manner, to the inside diameter of the body 326 of this embodiment. The strain relief 312 and catheter or multi-lumen tube 108 cooperate in the same manner as described in the prior embodiments.

Figure 13:
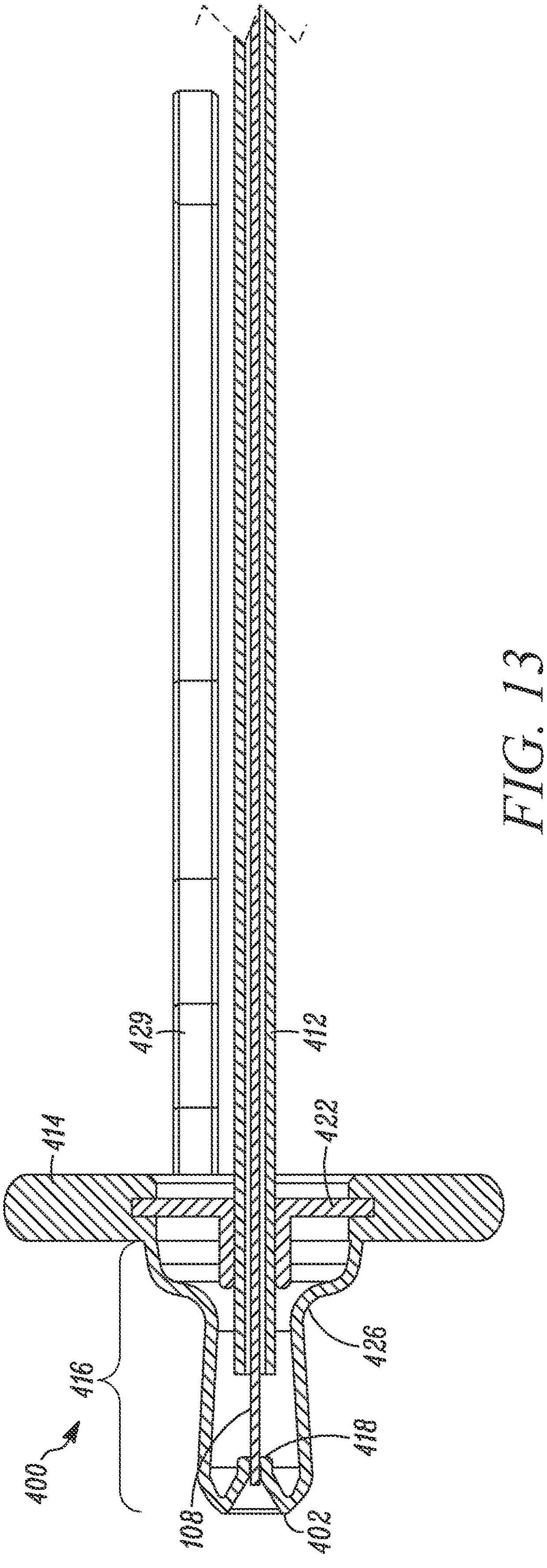
FIG. 13 is a cross-sectional view of a third alternative embodiment of the patient respiratory interface of FIG. 1.
Figure 14:
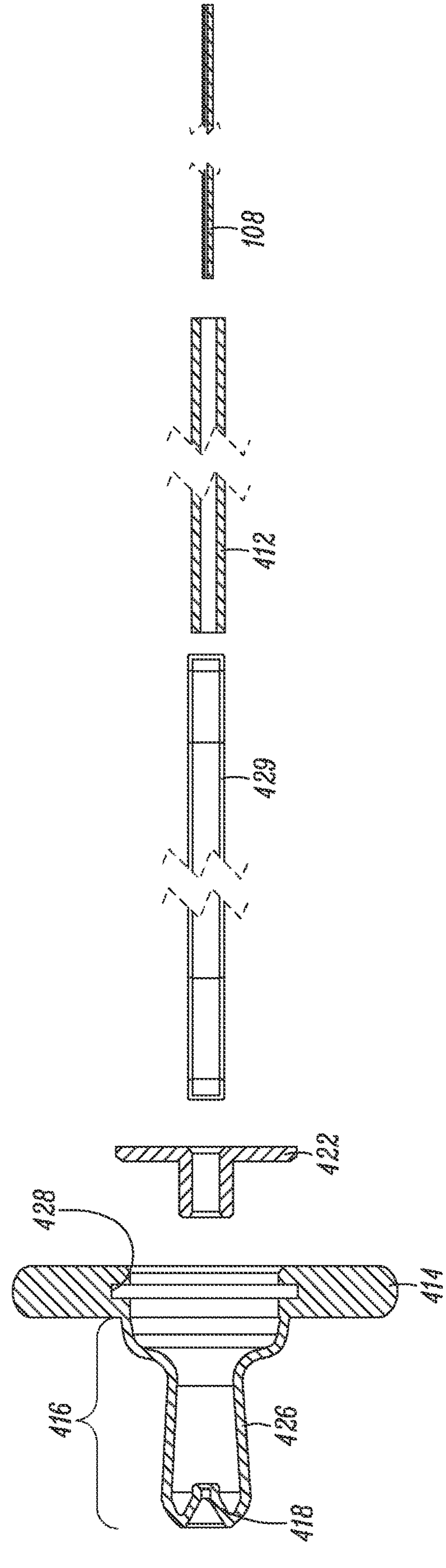
FIG. 14 is an exploded view of the patient respiratory interface of FIG. 14.
Figure 15B:
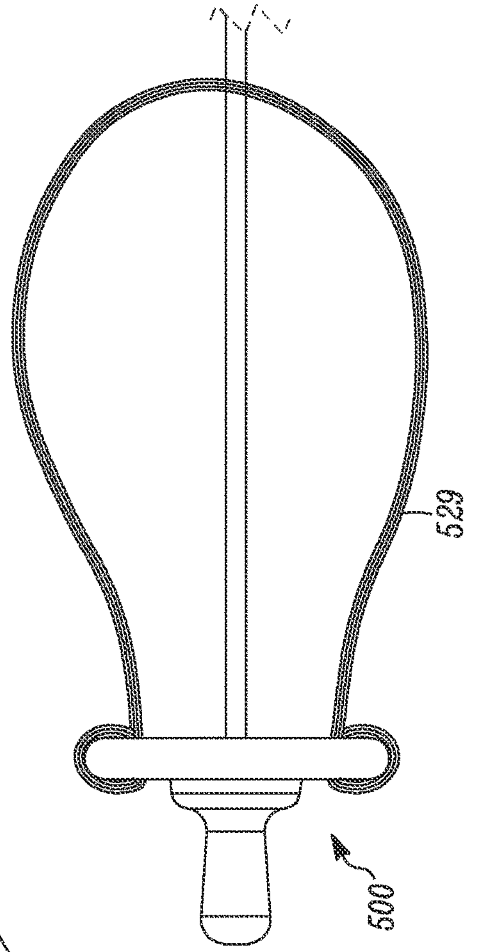
FIGS. 15A-15D illustrate front perspective (15A), top (158), side (15C) and front (15D) views of a fourth alternative embodiment of the patient respiratory interface of FIG. 1 having a retaining strap.
Figure 15D:
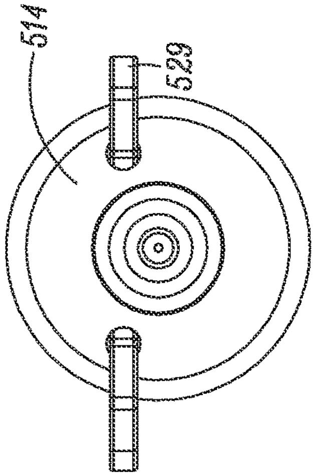
Figure 15A:
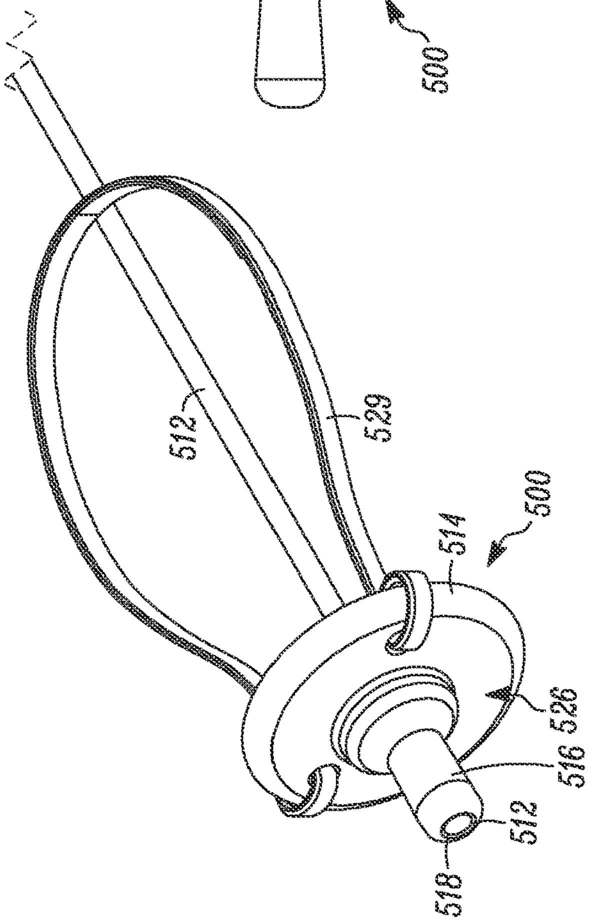
Figure 15C:
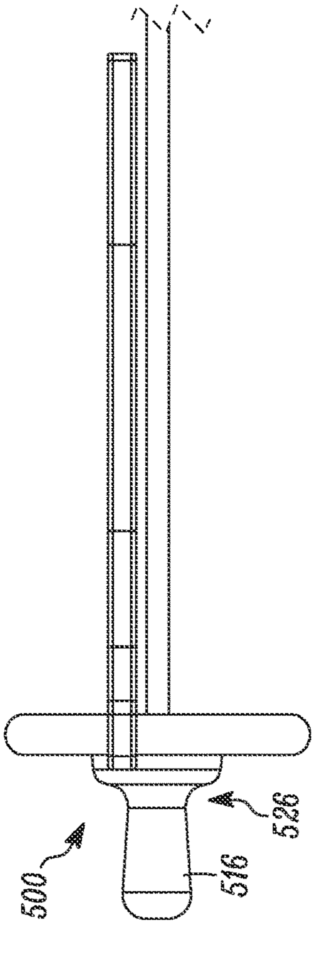

Referring to FIGS. 13 and 14, yet another embodiment of a patient respiratory interface 400 having a pacifier-shaped outer body 426 is disclosed. The interface 400 of FIGS. 13 and 14 includes an insertion portion 416 and flange 414 somewhat similar to that of FIGS. 1-9. Unlike the embodiment of FIGS. 1-9, inside the insertion portion 416 no retaining ring is used to maintain the shape of the tip of the insertion portion. The opening 418 for holding the multi-lumen tubing 108 is recessed within the tip 402 and receives the multi-lumen tubing or catheter in the same manner as that in FIGS. 1-9. A retaining sleeve fits 412 into a fastener and guide 422 in the same manner as described in the prior embodiments. An additional feature shown in FIGS. 13 and 14 is a partial view of a retaining strap 429 that attaches to the flange 414 of the interface 400 and can be stretched around the head of the patient to maintain the insertion member 416 in a desired position once on the patient. As shown in FIGS. 15A-15D, in the context of an interface 500 having a body 526 with a completely circular flange 514 and an insertion portion 516 similar to that of the embodiment of FIGS. 10-12, the retaining strap 529 is shown in greater detail. The retaining strap may be threaded through holes 509 within the flange 514 and extend to a diameter appropriate to elastically attach to a patient's head.

Figure 16:
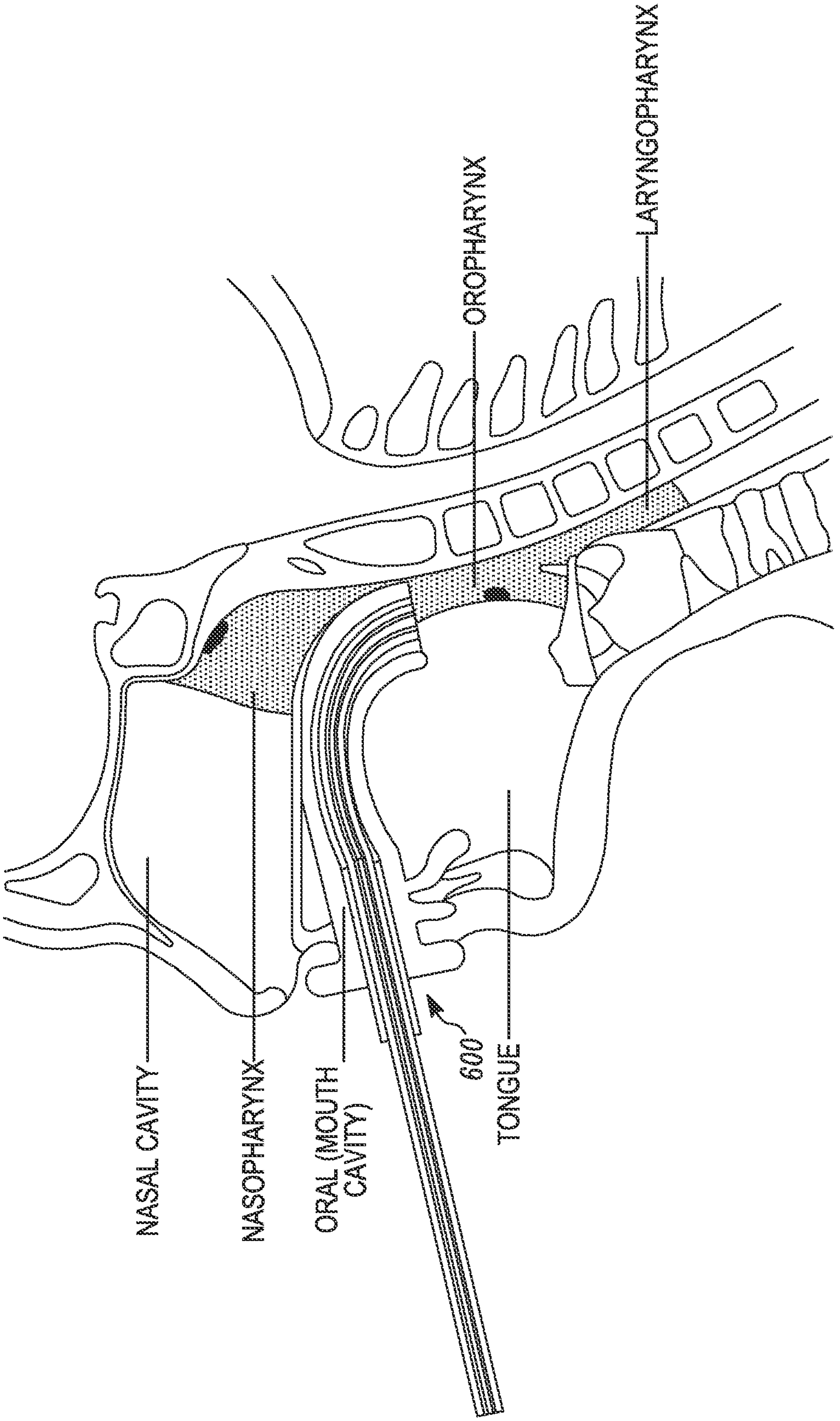
FIG. 16 illustrates a patient respiratory interface, having an alternative form to that of the pacifier-shaped embodiments of FIGS. 1-15, in relation to an anatomical cross-section of an upper respiratory system.
Figure 17B:
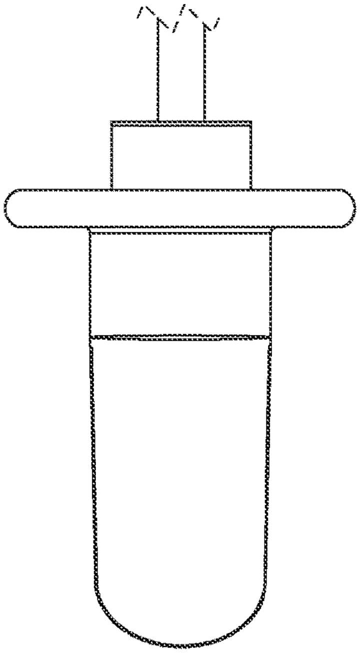
FIGS. 17A-17D illustrate front perspective (17A), top (178), side (17C) and front (17D) views of the patient respiratory interface of FIG. 16.
Figure 17D:
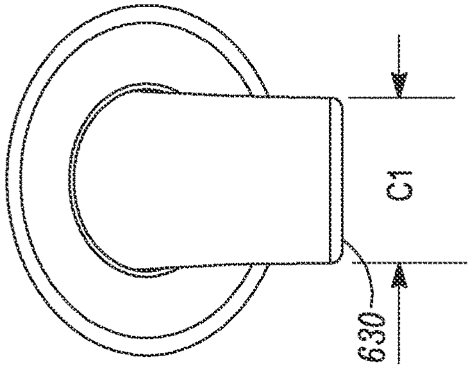
Figure 17A:
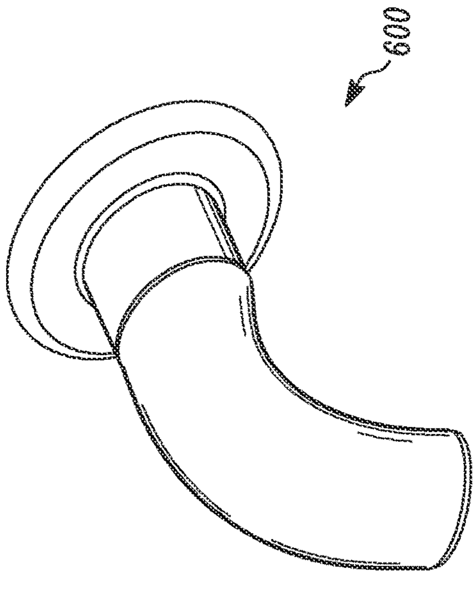
Figure 17C:
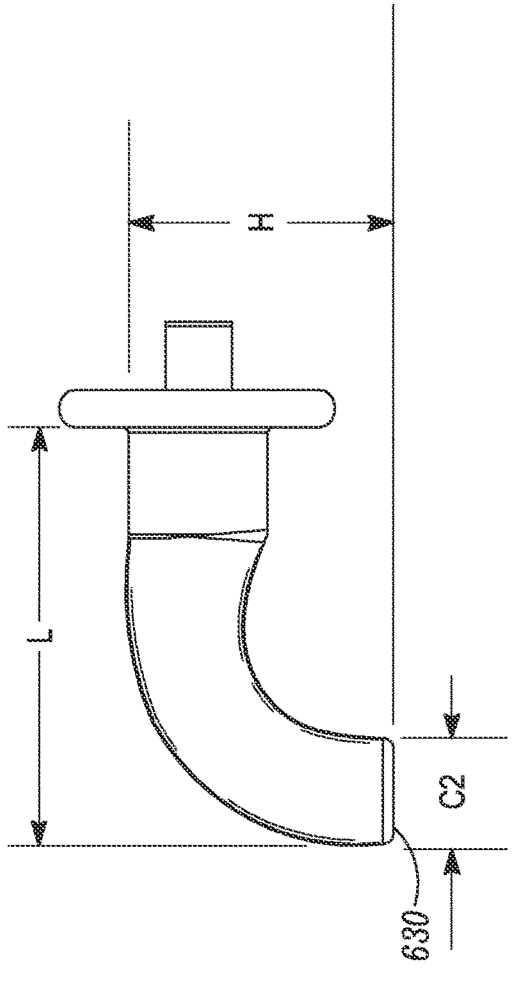
Figure 18B:
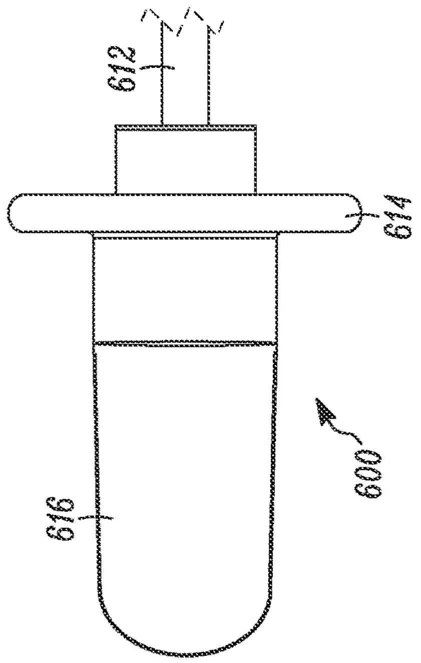
FIGS. 18A-18D illustrate front perspective (18A), top (188), side (18C) and front (18D) views of the patient respiratory interface of FIG. 16 including a strain relief sleeve and multi-lumen tubing.
Figure 18D:
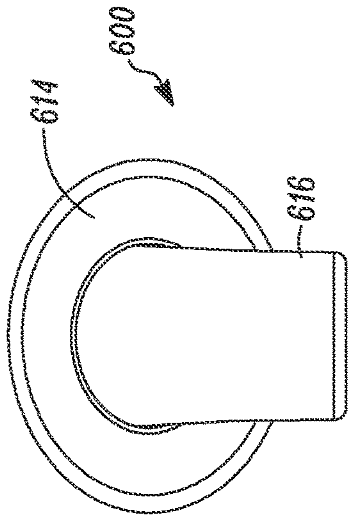
Figure 18A:
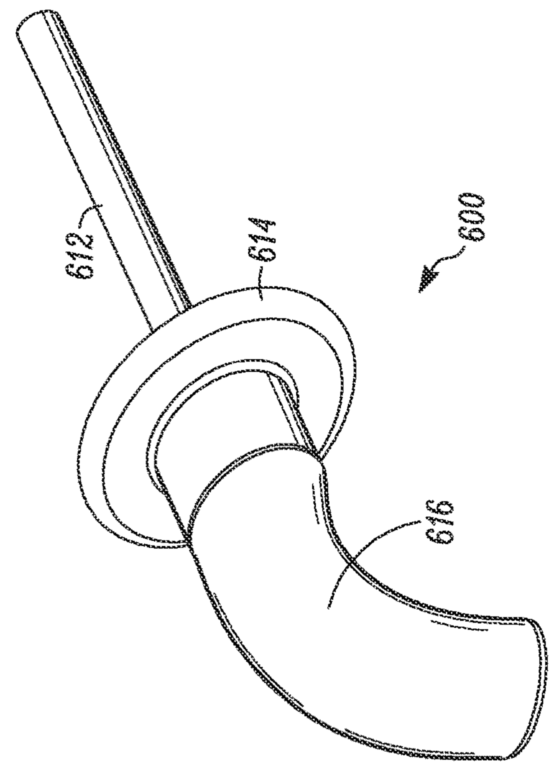
Figure 18C:
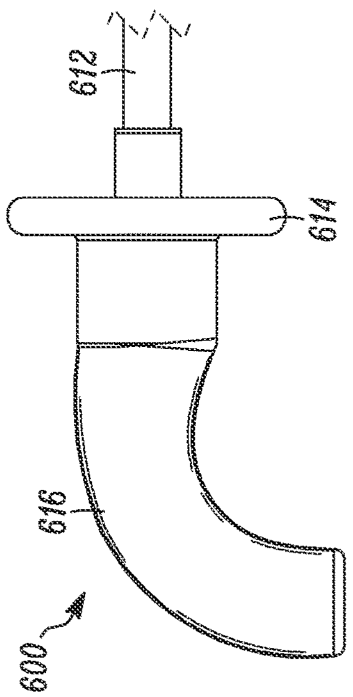
Figure 19:
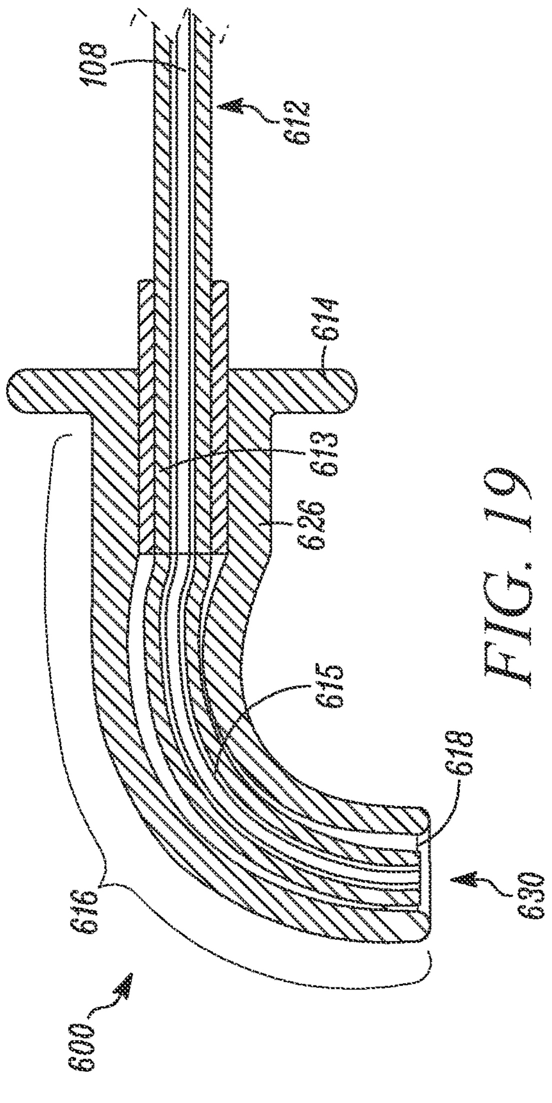
FIG. 19 is a cross-sectional view of the patient respiratory interface of FIG. 17C.
Figure 20:
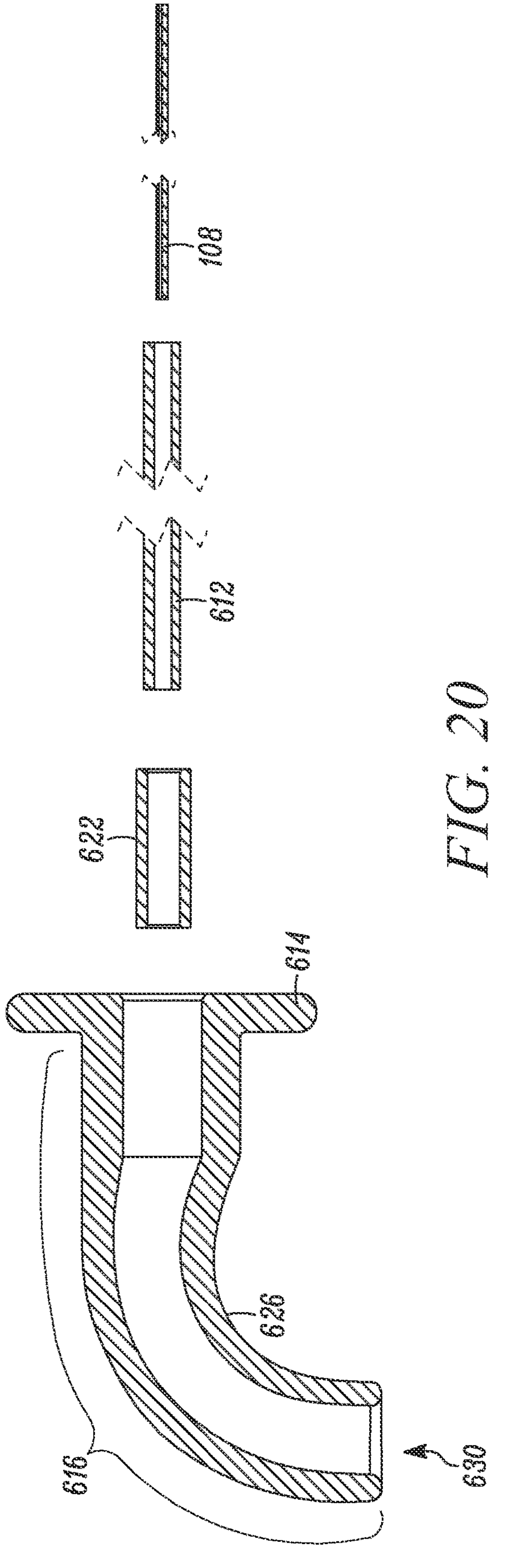
FIG. 20 is an exploded view of the patient respiratory interface of FIG. 19.

In other embodiments, such as shown in FIGS. 16-19, a more invasive interface is contemplated, where the interface may extend further into the patient's oropharynx than the shorter traditional pacifier-length versions of the prior figures. Referring now to FIG. 16, a curved respiratory interface 600 is shown positioned in a hypothetical patient's mouth. As is illustrated, the insertion portion extends past the oral cavity and curves down into the beginning to the oropharynx and is thus further into the patient's airway. FIGS. 17A-17D illustrate one example embodiment of the version of the interface shown in FIG. 16. Although not in the form of a pacifier as in prior embodiments, the interface 600 includes a flange 614 that limits the distance the insertion portion 616 may be inserted into the patient. As is seen, the insertion portion 616 forms a curved tube which generally follows the pathway of a patient's mouth and oral pharynx and extends further into a patient's airways. The shape of the opening 630 at the end of the outer body 626 of the interface 600 may be elliptical or circular. For example, as best illustrated in FIGS. 17C and 17D, one cross section (C1) of the opening 630 may be in the range of 10-13 mm, and the other cross section (C2) of the opening 630 may be in the range of 7-10 mm. In one embodiment, the length (L-FIG. 17C) of the insertion portion 616 perpendicular to the flange 614 may be in the range of 30-50 mm and the height (H) of the insertion portion may be 20-25 mm. Other combinations of dimensions are also contemplated depending on whether the patient is an adult, child or infant.

FIGS. 18A-18D and 19-20 show additional views of the embodiment of FIGS. 16 and 17A-17D with the strain relief sleeve 612 extending from the fastener and guide 622. The fastener and guide 622. The outer body 626 may be formed of a thermoplastic or PVC material and the fastener and guide of a thermoplastic resin or other rigid material. The insertion portion 616, which in this embodiment may also be referred to as an oral pharyngeal airway, of the body 626 is sized to extend past the oral cavity of an infant patient and may be anatomically sized for the passageway size and age of the infant patient. The strain relief sleeve 612 may be formed of a straight portion 613 and a curved portion 615 and may be a single piece or multiple pieces connectable at a junction between the straight and curved portions 613, 615. The strain relief sleeve 612 may be formed of a PVC or other rigid or flexible material and form a protective guide sized to receive and direct the multi-lumen tubing 108 to the patient's airways to deliver an aerosol produced by or carried by the multi-lumen tubing 108.

Figure 21:
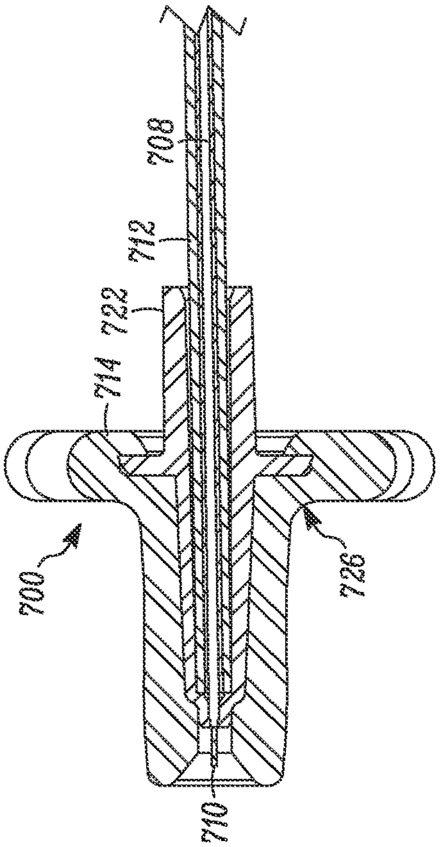
FIG. 21 is a cross-sectional view of an alternative embodiment of the patient respiratory interface of FIG. 1.
Figure 22:
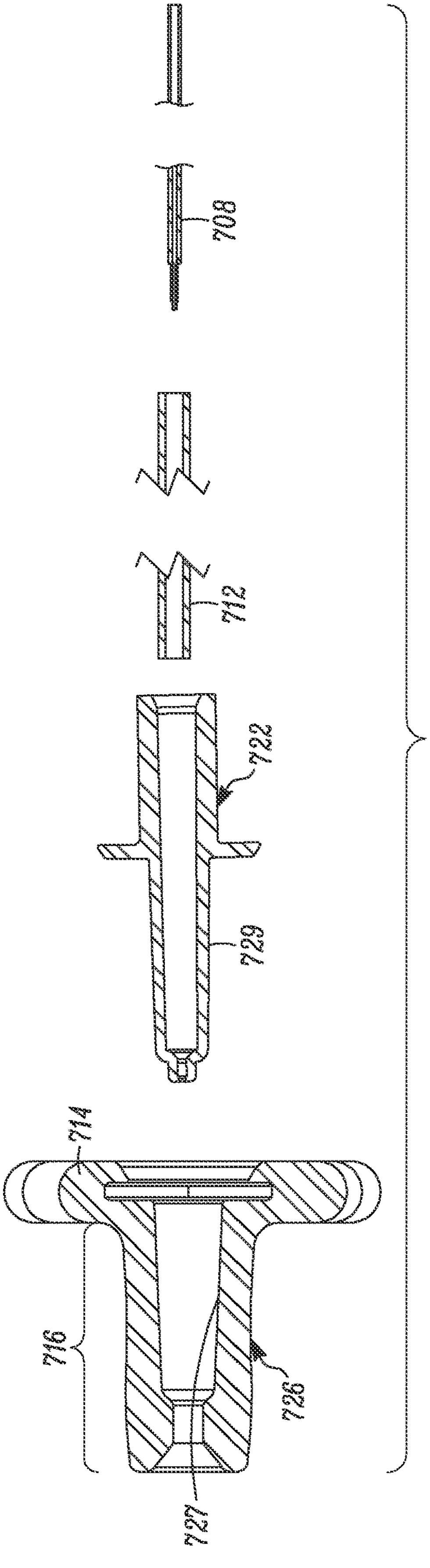
FIG. 22 is an exploded view of the patient respiratory interface of FIG. 21.
Figure 23:
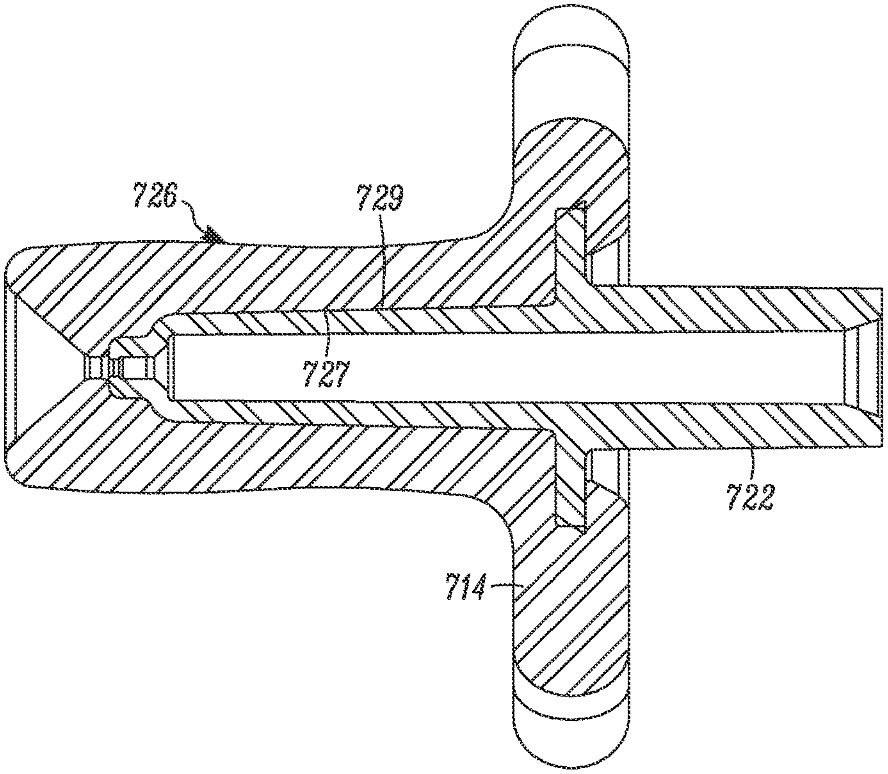
FIG. 23 is a cross-sectional view of the interface connector and outer body of FIGS. 21-22.

Referring now to FIGS. 21-23, an alternative embodiment of the patient interface 700 is shown. In this implementation of the interface 700, the insertion portion 716 of the soft, flexible body 726 is sized such that there a tighter fit between the inner surface 727 of the passageway through the body 726 and the outer surface 729 of the interface connector 722, also referred to as the fastener and guide. As best seen in FIG. 21, the inner surface 727 of the passageway in the body 726 forms a close fit with the outer surface 729 of the interface connector 722. In one implementation, the clearance between the inner surface 727 and the outer surface 729 is approximately 0.05 mm along the length of the inner surface 727 and outer surface 729. As noted previously with respect to other embodiments, the body 726, or at least the insertion portion 716, may be constructed of a soft pliable material such as silicone. The interface connector 722 may be constructed of a rigid material such as plastic or thermoplastic resin material.

Figure 24:
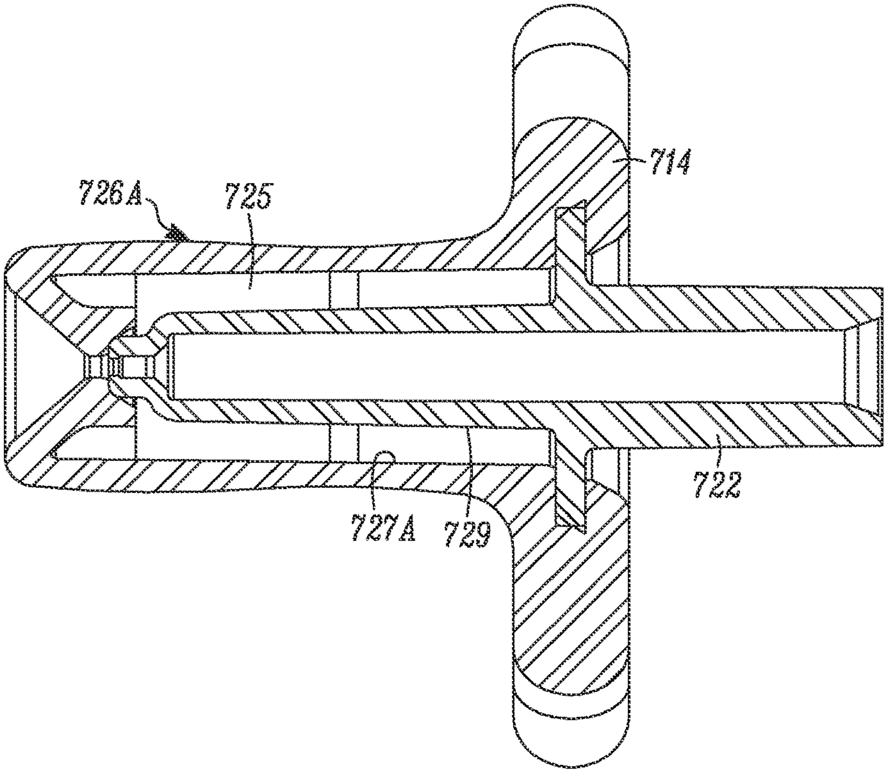
FIG. 24 is a cross-sectional view of an alternative configuration of interface and outer body of FIG. 23.
Figure 25:
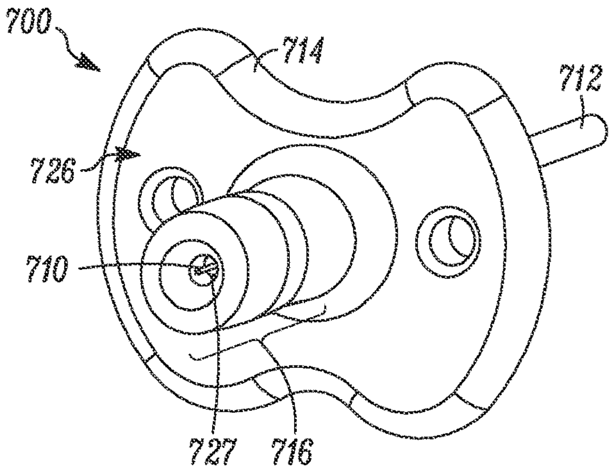
FIG. 25 is a perspective view of the patient respiratory interface of FIG. 21.

In one embodiment, referring to FIG. 24, the clearance between the inner surface 727A of the passageway in the body 726, and outer surface 729 of the interface connector 722 may allow for a gap 725 or loose fit such where the interface connector clearance to the inner surface of the insertion portion is approximately 1.8 mm to 3.15 mm (or greater in other implementations) to allow greater flexibility and more of a traditional pacifier feel to an infant using the interface 700. In other embodiments, such as best illustrated in FIGS. 21-23, the clearance may be 0.05 mm or less. The reduction in clearance between the inner wall of the insertion portion of the body and the outer surface of the interface connector may be accomplished by thickening the soft material wall of the insertion portion 716, thickening the wall of the interface connector 722, or a combination of both. By utilizing a tight fit between the two components, lateral and angular movement of the insertion portion 716 and the body 726 generally may be limited. This limit of lateral and angular movement of the insertion portion 716 relative to the interface connector 722 may, in turn, prevent potential contact between the tip 710 of the catheter 708 and the inside surface 727 near the tip of the insertion portion 716 of the body 726 (See FIG. 25). In one embodiment, to compensate for the added material thickness and rigidity of the flexible body 726, the material durometer of the flexible body 726 may be decreased in order to soften the insertion portion 716 of the assembled neonatal interface 700. For example, in embodiments with greater clearance between interface connector 722 and inner surface 727 of the body 726 (See FIG. 24), or where the interface connector 722 does not extend as far along the insertion portion 716 of the body 726 as is shown in FIGS. 21-23, the durometer may be in the range of 55 to 65 Shore A hardness with a nominal value of 60 Shore A hardness. For embodiments where the body 726 of the patient interface 700 has a smaller clearance between body 726 and interface connector 722, for example 0.05 mm or less, the body 726 may have a durometer in the range of 35 to 50 Shore A, with a nominal hardness of 45 Shore A.

Figure 26A:
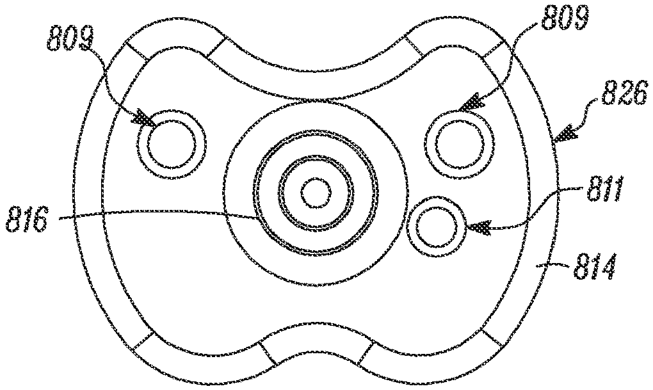
FIGS. 26A-26B illustrate front (26A) and perspective (268) views of an alternative embodiment of the outer body of the patient respiratory interface of FIG. 25.
Figure 26B:
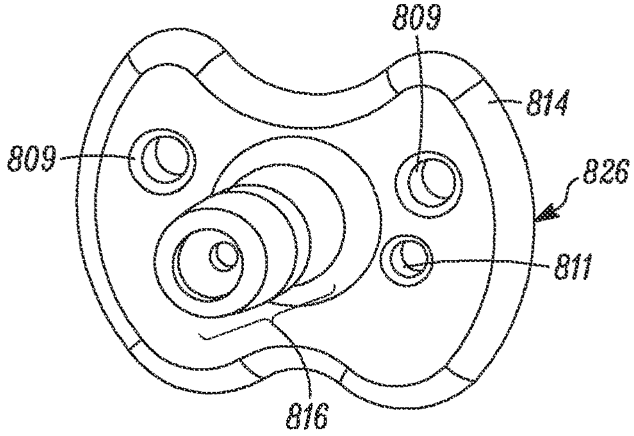
Figure 27A:
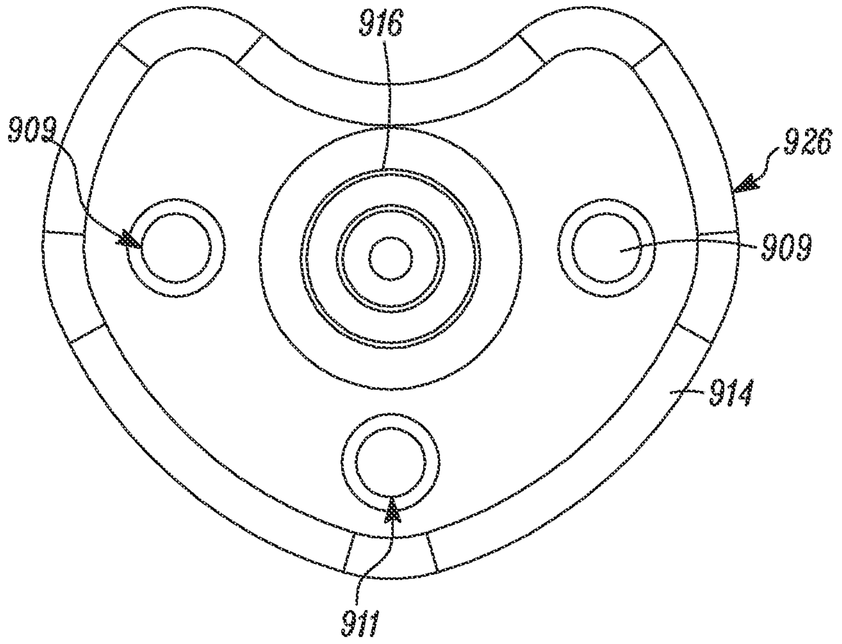
FIGS. 27A-27B illustrate front (278) and perspective (27A) views of an alternative embodiment of the outer body of the patient respiratory interface of FIGS. 26A-26B.
Figure 27B:
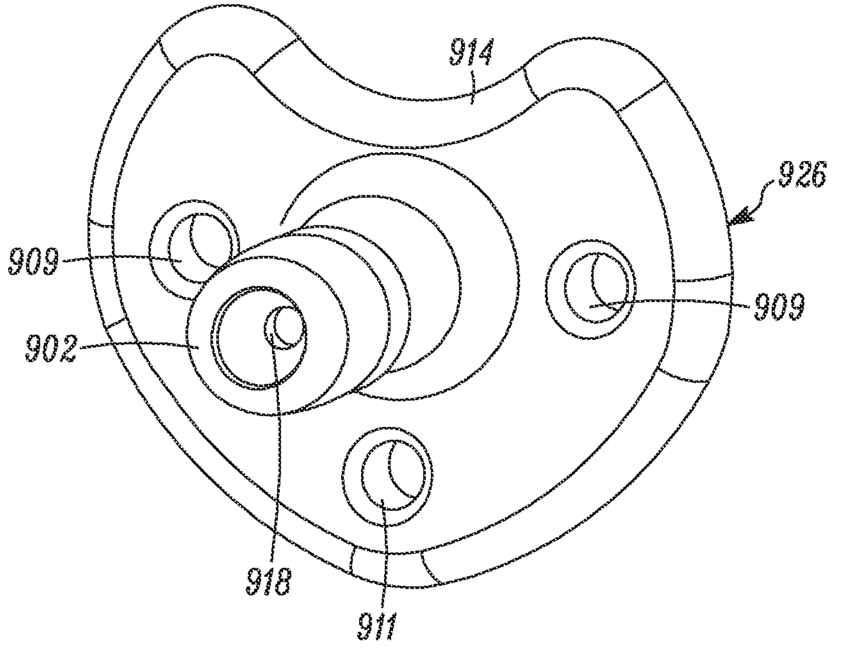
Figure 28A:
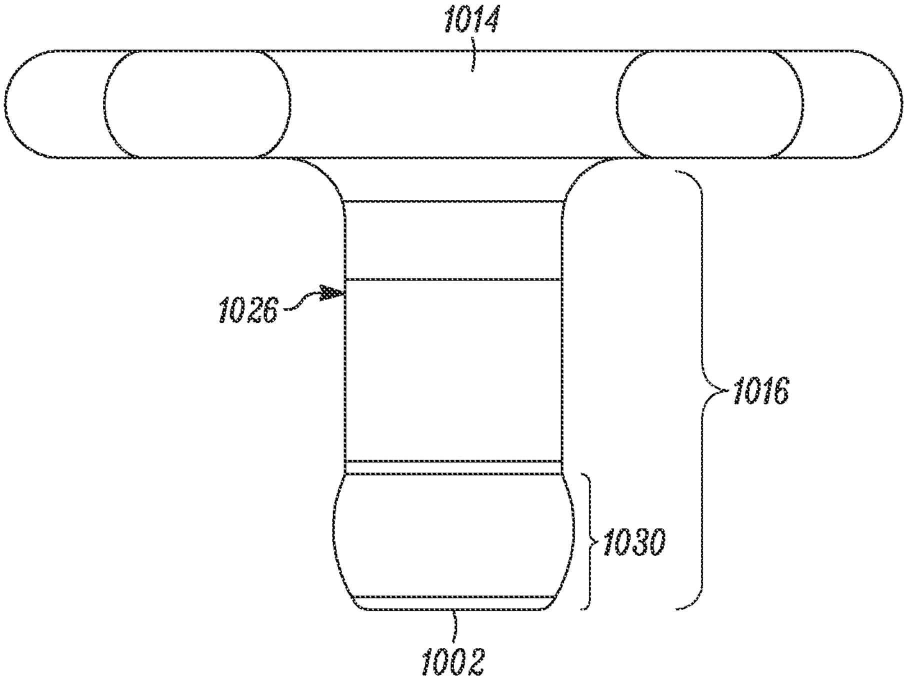
FIGS. 28A-28D illustrate top (28A), front perspective (28B), front (28C) and perspective (28D) views of an alternative embodiment of the outer body of the patient respiratory interface of FIG. 25 including an enlarged tip.
Figure 28B:
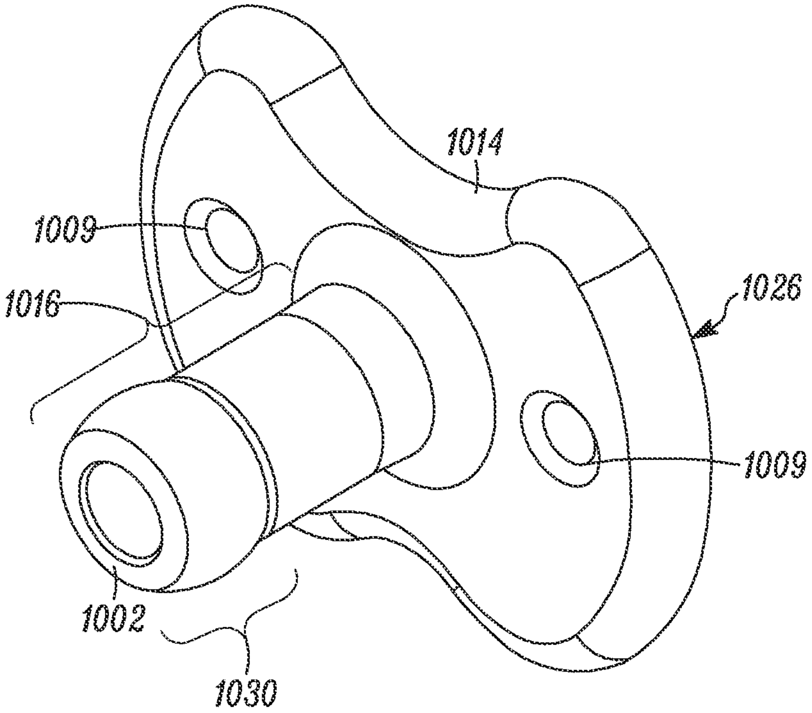
Figure 28C:
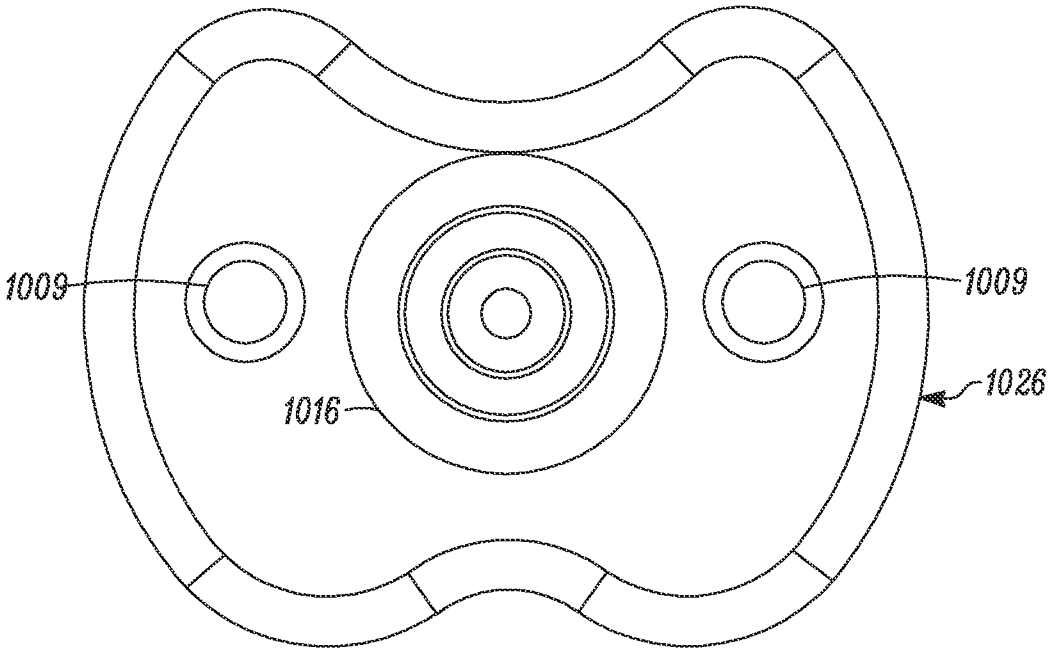
Figure 28D:
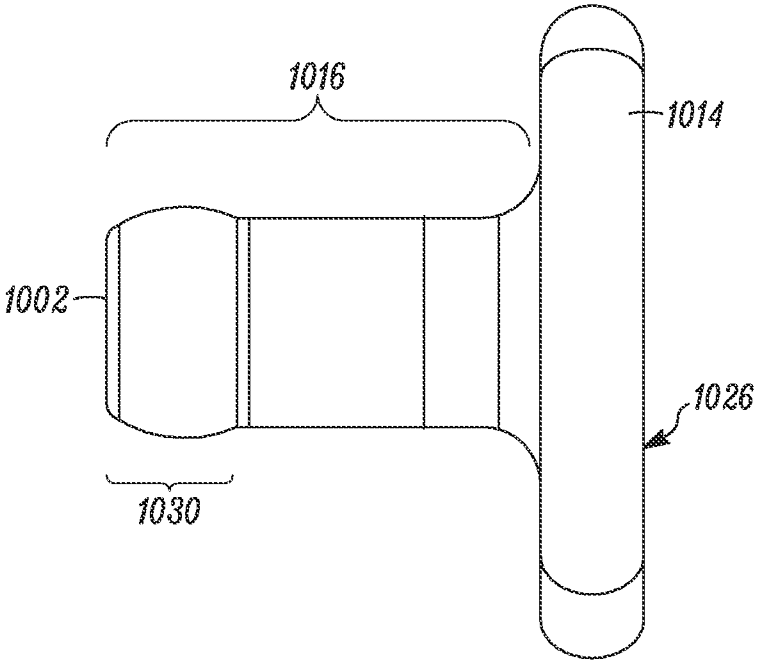

Additional features and embodiments of a patient interface are illustrated in FIGS. 26A-26B. In addition to openings 809 for receiving a tie strap (not shown) in the flange portion 814 of the outer body 826 of the neonatal interface, the flange portion 814 may also define a suction catheter port 811. The suction catheter port 811 may be located to the left or the right of the insertion portion 816, generally in proximity of one of the openings 809 for the tie strap that may be used to place around an infant's head to hold the patient interface against the face of the infant (see example tie strap 529 in FIG. 15A). Alternatively, as shown in FIGS. 27A-27B, the outer body 926 may use a different shaped flange 914 having greater surface area underneath the insertion portion 916 within which to locate a suction tube port 911. The suction port 911 may have a diameter sized to slidably accept a suction lumen so that, while an assembled patient interface with centrally positioned catheter is supplying an aerosolized medicament, or partially aerosolized medicament, through the centrally located opening 918 at the tip 902 of the insertion portion 916, a separate suction catheter may be concurrently positioned in the suction catheter port 911 to suction out excess liquid from the mouth of the infant.

In another alternative embodiment, as shown in FIGS. 28A-28D, the outer body 1026 of the patient interface may be formed with a nipple geometry, in other words the shape of the end region 1030 of the insertion portion 1016, enlarged to achieve increased infant latching on the patient interface. The enlargement of the end region 1030 may be a thickening of the same flexible material that makes up the rest of the insertion portion 1016 of the outer body 1026, or it may be made up of a same or different material attached to the end of the insertion portion 1016. The increased thickness is preferably sufficient to allow an infant to latch on to the insertion portion 1016 without causing discomfort. The enlarged diameter end region 1030 may increase in diameter from the beginning of the region 1030 positioned closest to the flange 1014 side of the region to a maximum diameter in approximately the center of the end region and then taper down to a diameter less than the maximum diameter at the tip 1002 end of the end region 1030. The end region 1030 may be rounded as shown in FIGS. 28A-28D or it may be formed of a more abrupt or squared-off geometry with angled or stepped changes between the diameter of the insertion portion 1016 nearer to the flange and the beginning of the end region 1030. In other implementations, the end region 1030 may have its greatest diameter at the tip 1002 or at the flange side of the end region 1030.

It is contemplated that any of features of the patient interface embodiments discussed in FIGS. 1-28 may be combined in different embodiments. For example the outer body 1026 with the feature of an interior surface 727, 727A (FIGS. 23 and 24) that forms a tight fit or a loose fit with an interface connector 722, respectively, along with the associated variations in hardness. The use of openings 1009 for a restraining strap may or may not be included and one or more of a suction port 811 (FIGS. 26A-26B) and a pressure relief assembly 215 (FIGS. 8-9) may be included. These combinations are simply provided by way of example and other combinations of the disclosed features are also contemplated.

Additionally, the patient interface 700 and variations of FIGS. 21-28D may be part of an aerosol delivery system that uses the patient interface 700 to provide the desired aerosol treatment to an infant or other suitable patient. For example the patient interface may be part of the aerosol delivery system 104 of FIG. 2, replacing the version of the patient interface 100 shown there. Similarly, it is contemplated that any of the variations of the patient interface disclosed in FIGS. 1-28 may be combined with the aerosol delivery system 104 of FIG. 2.

Referring now to FIGS. 29-34, versions of a patient interface 1100, 1200 are illustrated where an expansion chamber 1122, 1222 may be attached to the outer body 1126, 1226 in place of in insertion portion 722 (FIGS. 21-22). The expansion chamber 1122, 1222 would allow aerosol droplets generated by the catheter 1108, 1208 to reduce in velocity and particle size prior to entering the hollow passageway 1129, 1229 of the insertion portion 1116, 1216. The volume of the chamber 1122, 1222 may be in the range of 30 ml to 150 ml in one implementation. Each of the chamber 1122, 1222 include a guide 1123, 1223 sized to receive a strain relief tube 1112, 1212 and allow a catheter 1108, 1208 to extend into the chamber when assembled.

Figure 29:
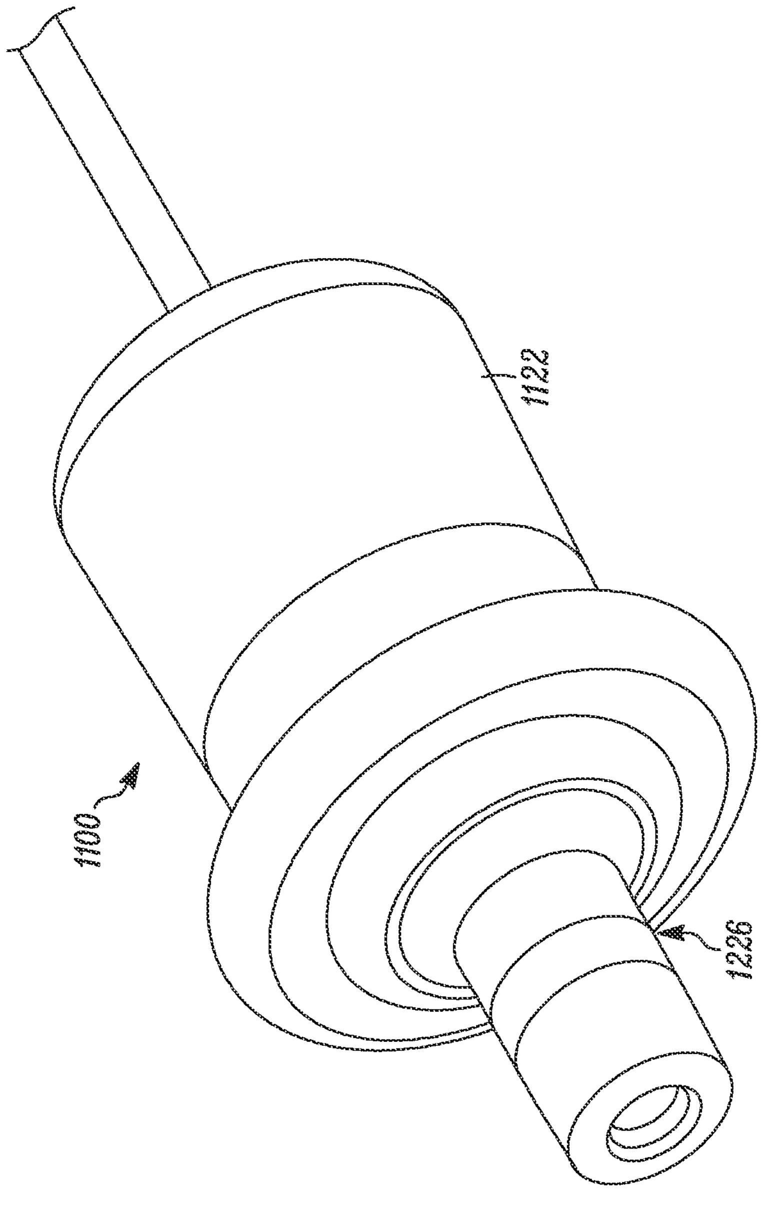
FIG. 29 is a perspective view of a patient respiratory interface having an expansion chamber.
Figure 30:
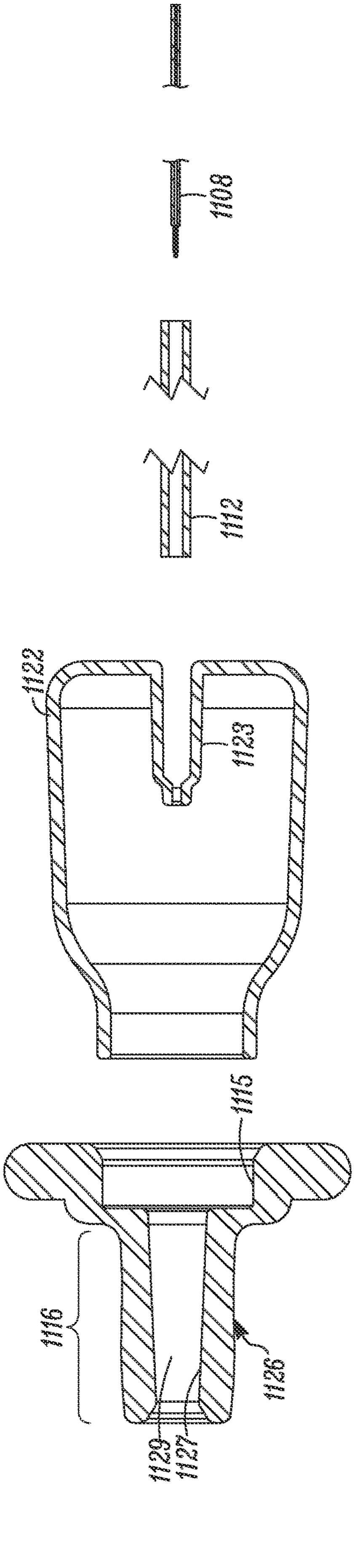
FIG. 30 is a cross-sectional, exploded view of the patient respiratory interface of FIG. 29.
Figure 31:
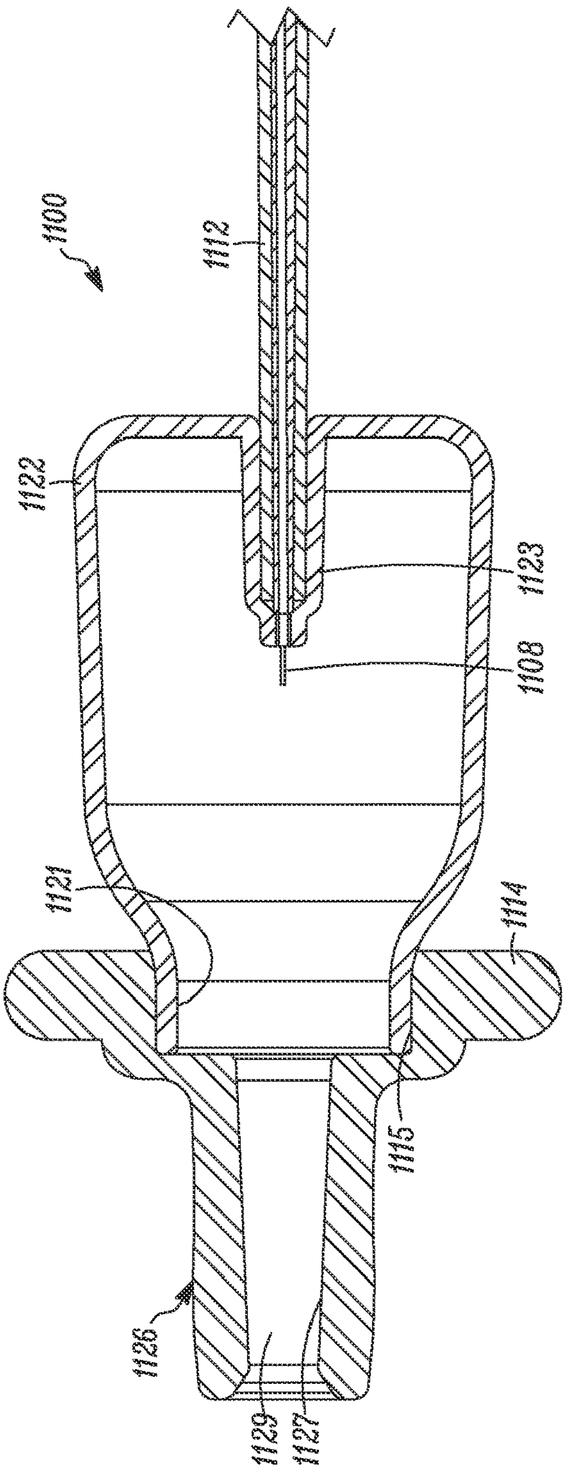
FIG. 31 is a cross-sectional view of the patient respiratory interface of FIG. 29.
Figure 32:
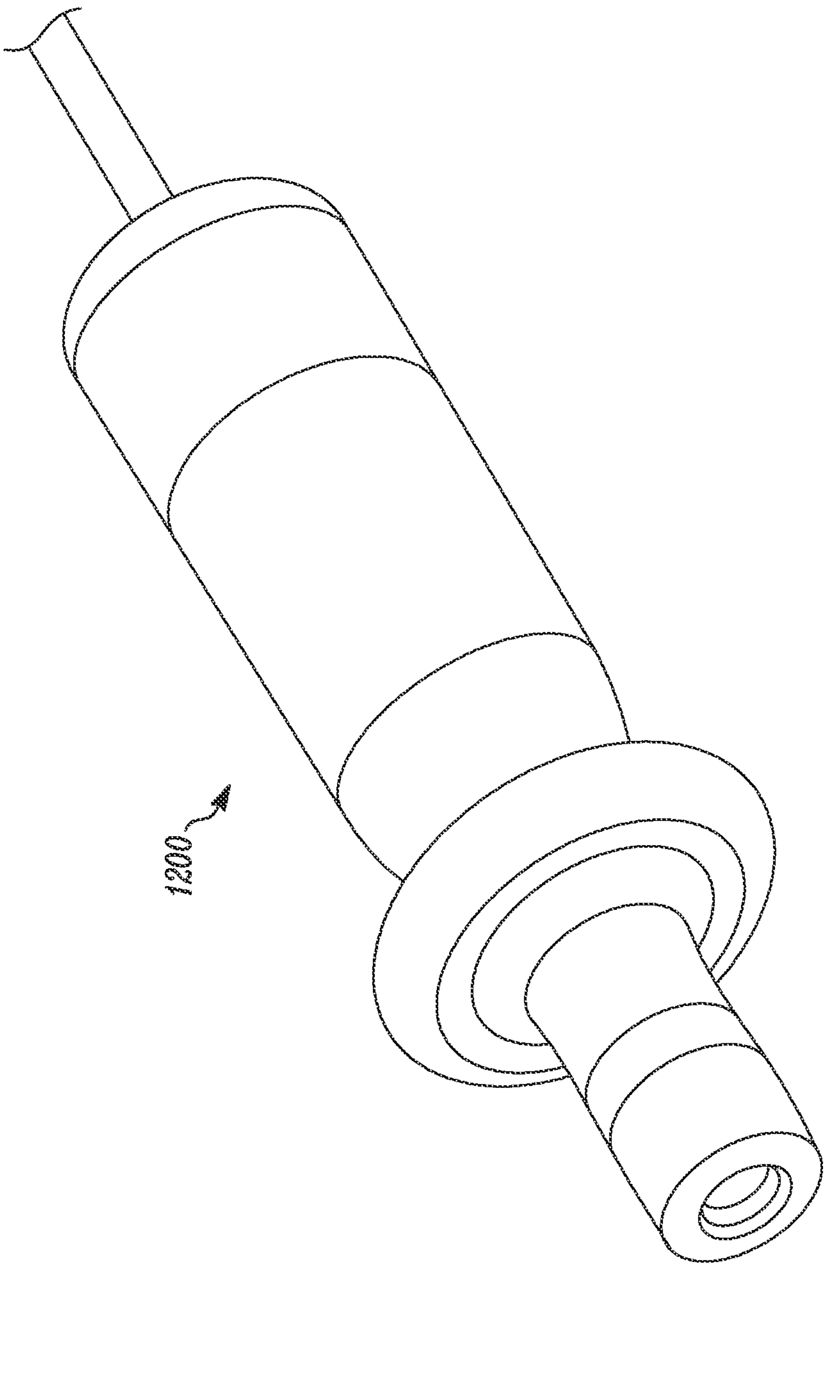
FIG. 32 is a perspective view of an alternate embodiment of the respiratory interface of FIG. 29.
Figure 33:
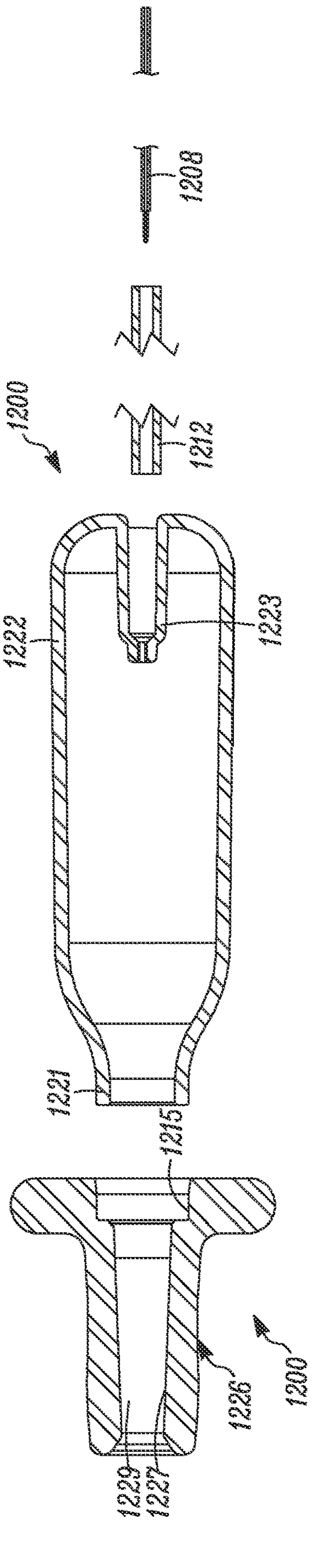
FIG. 33 is a cross-sectional, exploded view of the patient respiratory interface of FIG. 32.
Figure 34:
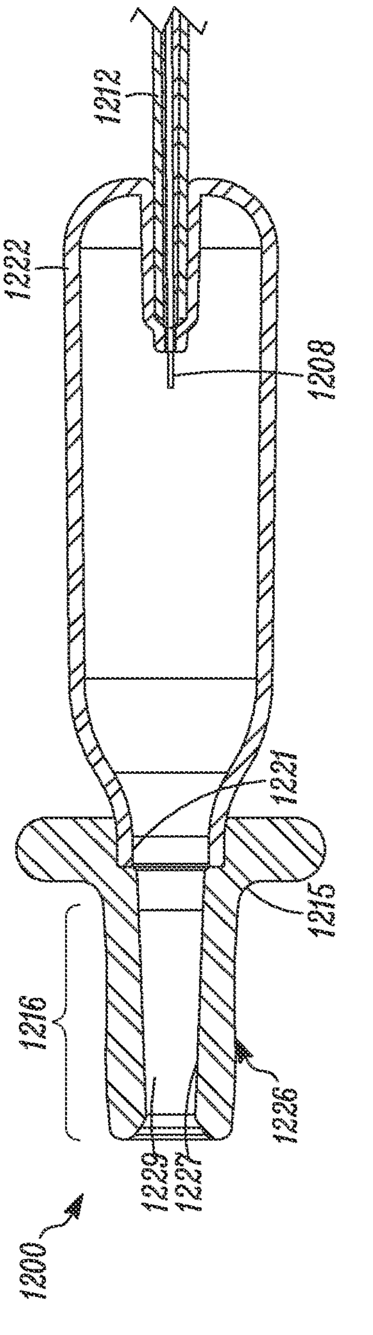
FIG. 34 is a cross-sectional view of the patient respiratory interface of FIG. 32.
Figure 35A:
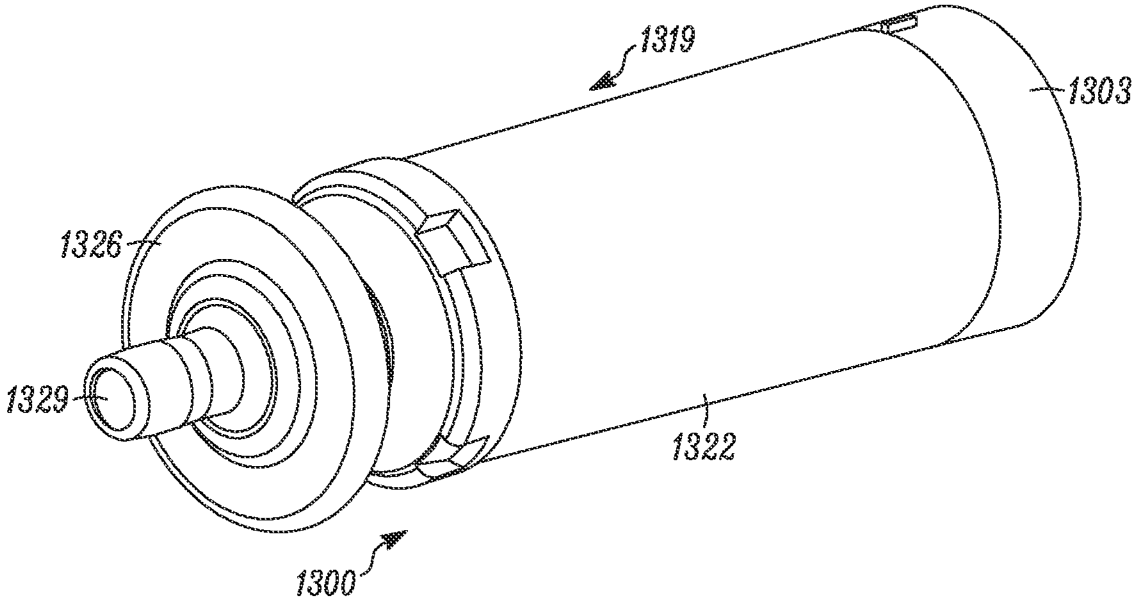
FIGS. 35A-35D are front perspective (35A), rear perspective (35B), side (35C) and exploded (35D) views of a patient respiratory interface including a valved holding chamber.
Figure 35B:
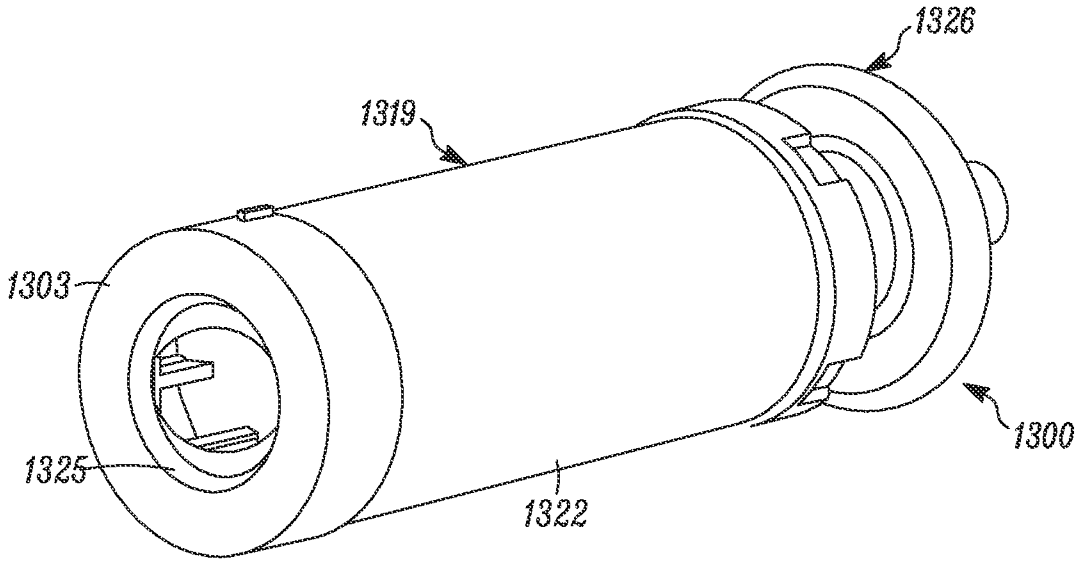
Figure 35C:
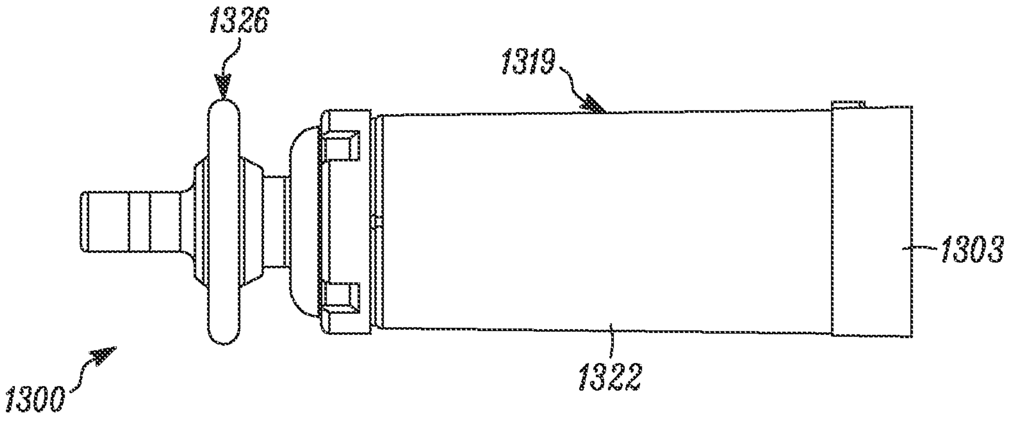
Figure 35D:
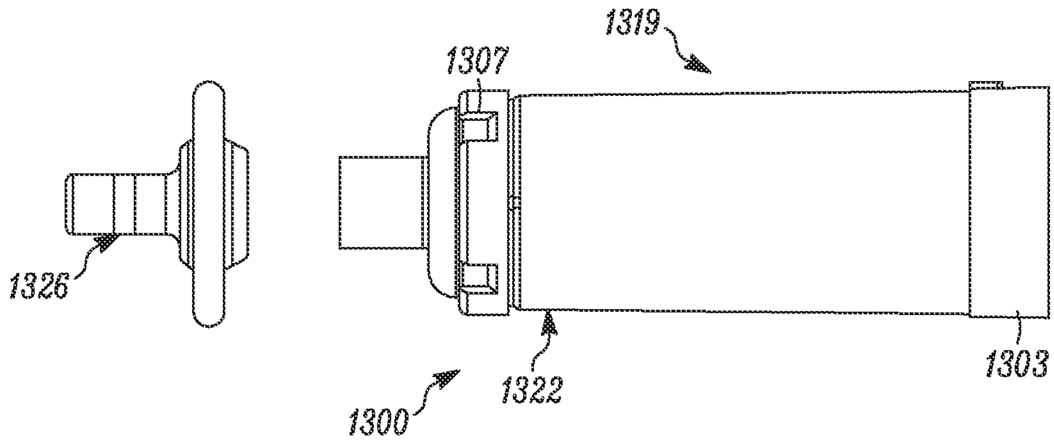

The embodiment of FIGS. 29-31 illustrates a chamber 1122 having a shorter and wider profile than the embodiment of FIGS. 32-34. In the patient interface 1100 of FIGS. 29-31, the wider chamber is combined with a wider mouth 1121 that fits into a receiving opening 1115 in the flange 1114 of the outer body 1126. The receiving opening 1115 and mouth 1121 are sized to form a friction fit in one embodiment. Other connection means may be acceptable, such as a snap fit. Also, the passageway 1129 of the insertion portion 1116 is kept at a wider diameter than in other embodiments such as shown in FIGS. 21-22 to reduce impact of aerosol formed further away in the chamber 1129 unlike the aerosol that is formed nearer to the tip as in the embodiment of FIGS. 21-22. The interior walls 1127 of the passageway in the insertion portion 1116 may be tapered toward the tip of the insertion portion. In contrast to the version of FIGS. 29-31, the patient interface 1200 with expansion chamber 1222 of FIGS. 32-34 is shown with a longer length and narrower diameter. Accordingly, a smaller opening 1215 and mouth 1221 may be implemented. As with the embodiment of FIGS. 29-31, the passageway 1229 and interior wall 1227 of the insertion portion 1216 may be sized to provide minimum obstruction to the aerosol being drawn into a patient's mouth when aerosol is being generated and the insertion portion 1216 of the interface 1200 is positioned in a patient's mouth.

Figure 36A:
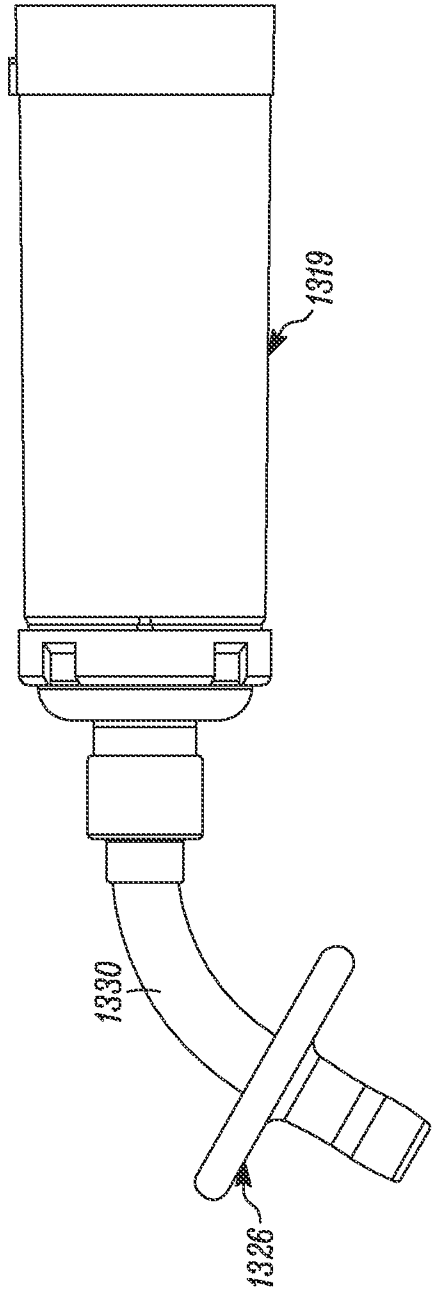
FIGS. 36A-36B are side (36A) and exploded (388) views of an alternative embodiment of the patient respiratory interface of FIGS. 35A-35D.
Figure 36B:
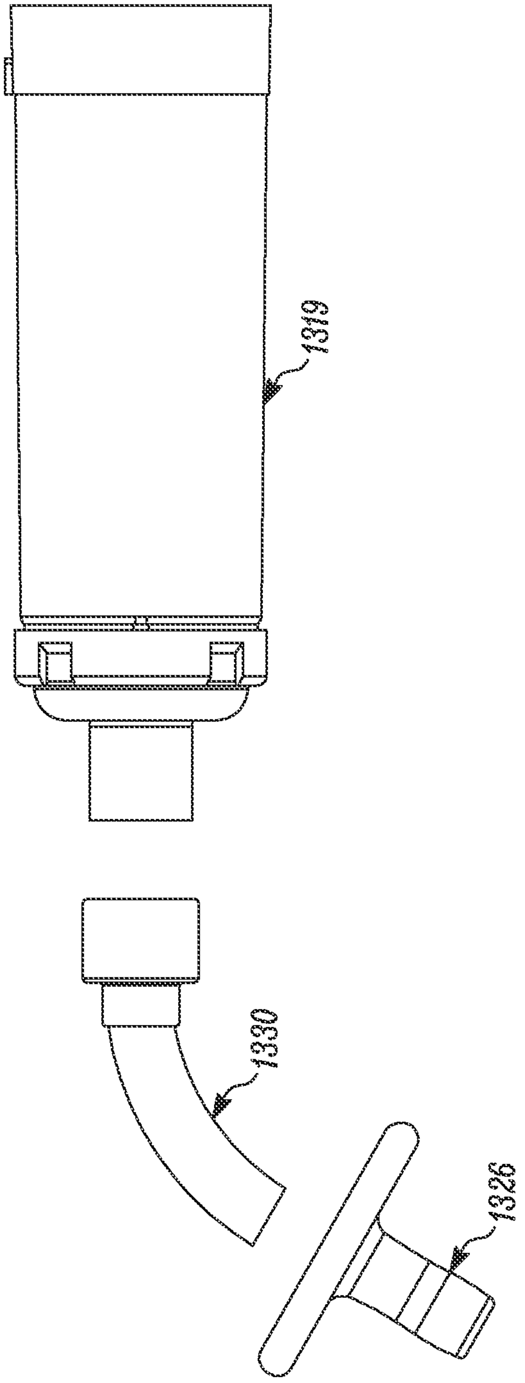
Figure 37A:
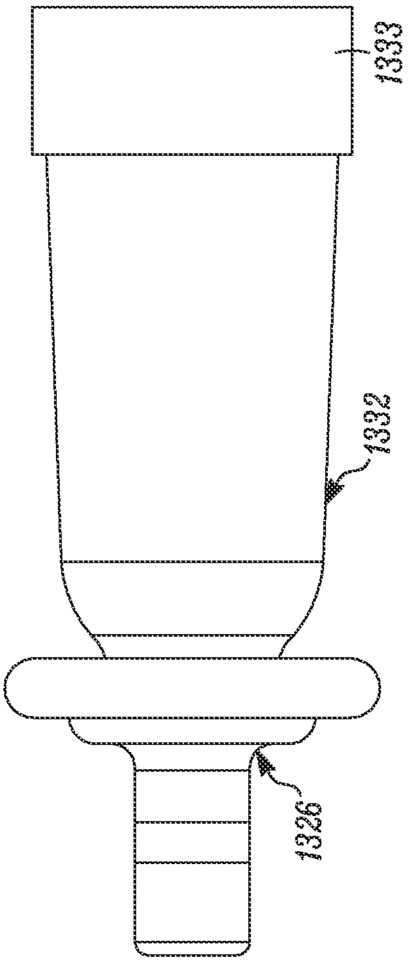
FIGS. 37A-37B are side (37A) and exploded (378) views of an alternative embodiment of the patient respiratory interface of FIGS. 36A-36B.
Figure 37B:
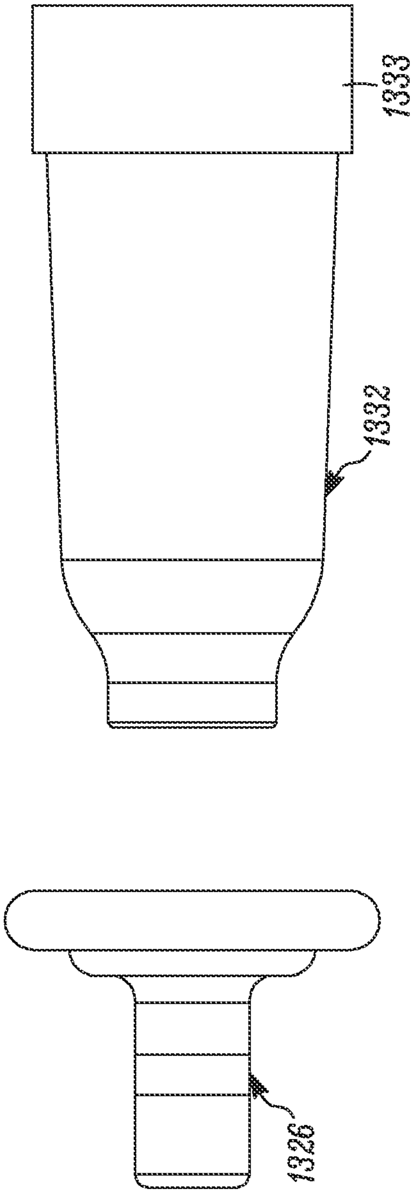

Referring now to FIGS. 35A-35D, another use of the patient interface 1300 is illustrated. The outer body 1326 shaped in the pacifier shape of any of the previously illustrated versions may be adapted to fit on an end of a valved holding chamber 1319 that may be used with a metered dose inhaler (not shown) to deliver medication via the central opening 1329 in the pacifier-shaped outer body 1326. Thus instead of an aerosol delivery system 104 such as in FIG. 2, a self-contained metered dose inhaler would connect to a rear adapter 1303 having an opening 1305 sized to receive the metered dose inhaler and allow expelled aerosolized medicament to expand in the expansion chamber 1322. A one-way valve and/or baffle may be positioned in the end cap 1307 assembly of the valved holding chamber 1319. As shown in FIGS. 36A and 368, to permit the valved holding chamber 1319 to be used with a reclining or supine patient, a connecting tube or elbow 1330, which may be rigid, flexible or articulated in different implementations, may be positioned between the valved holding chamber 1319 and the outer body 1326. A version of a holding chamber 1332 and pacifier-shaped outer body 1326, where the holding chamber 1332 is without a valve is illustrated in FIGS. 37A and 37B. The holding chamber would be without the valve of the prior example chamber, but would include a rear connector 1333 sized to receive a metered dose inhaler. Any of a number of holding chambers may be used in this embodiment. An example of one suitable holding chamber may be found in U.S. Patent Pub. No. 2014/0116436, published May 1, 2014 and entitled "Medication delivery apparatus and system and methods for the use and assembly thereof", the entirety of which is hereby incorporated herein by reference.

Figure 38A:
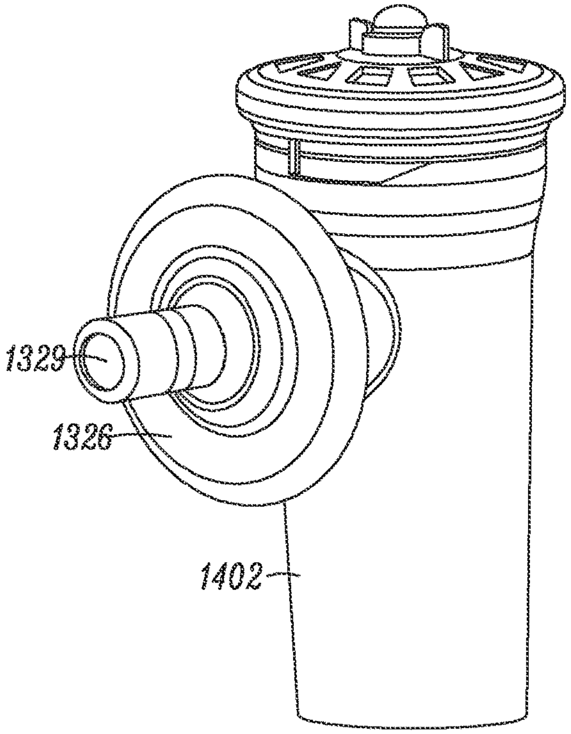
FIGS. 38A-38B are front perspective (38A) and side exploded (388) views of a patient respiratory interface including a nebulizer device.
Figure 38B:
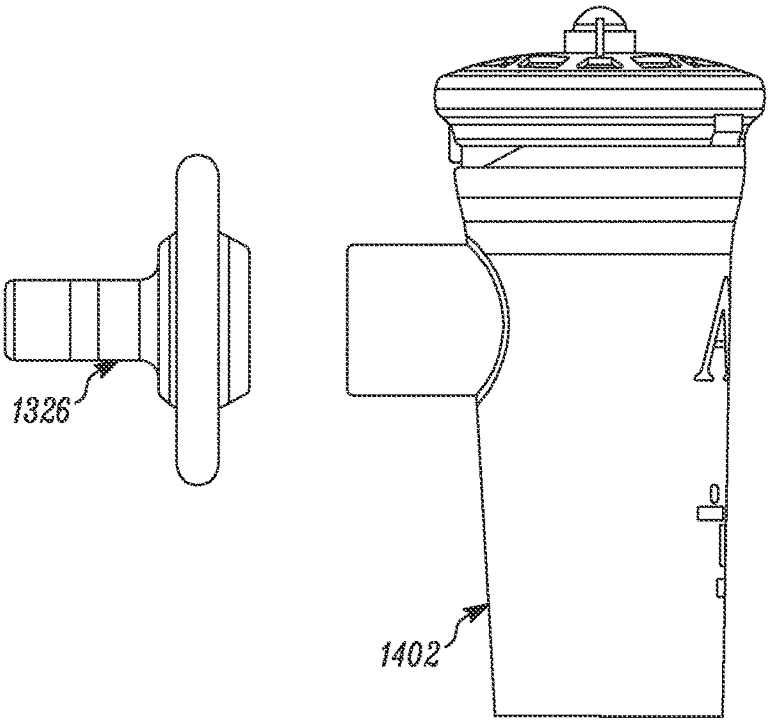
Figure 39A:
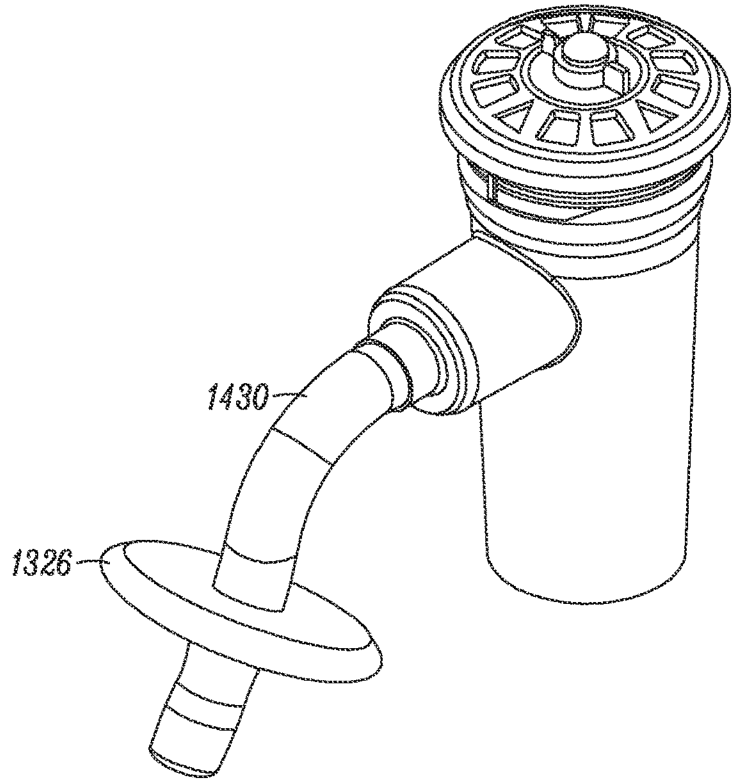
FIGS. 39A-39B are front perspective (38A) and side exploded (388) views of the patient respiratory interface including a nebulizer device of FIGS. 38A-38B with a connecting tube.
Figure 39B:
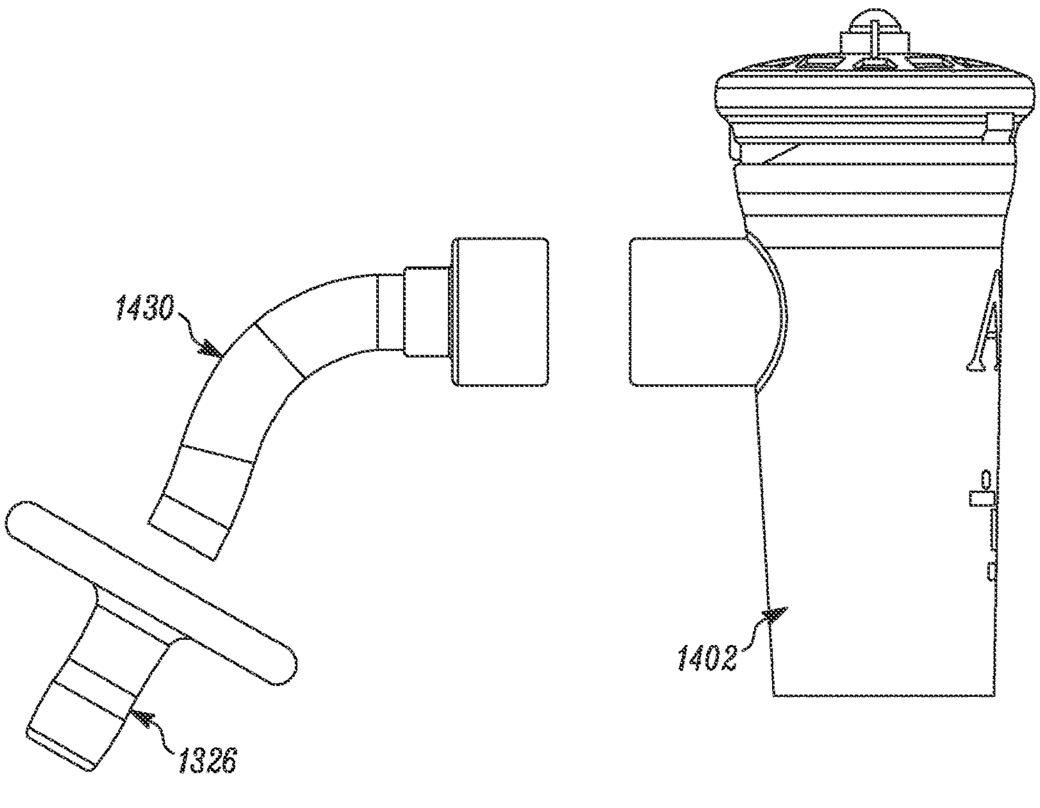

Other aerosol delivery systems may also be coupled with the patient interface having the central opening for permitting aerosolized medicament to enter a patient's mouth. For example, a nebulizer 1402 may be removably coupled with the pacifier-shaped outer body 1326 to permit delivery of an aerosol locally generated in the nebulizer 1402 to be withdrawn by a patient through the central opening 1329 at the end of the outer body. The pacifier-shaped outer body of the patient interface may be directly connected to the output of the nebulizer as shown in FIGS. 38A and 388, or it may be used with a curved connecting tube or elbow 1430 that connects the nebulizer 1402 to the outer body 1326 and allows the nebulizer to remain upright in situations where the patient is reclined or lying down in a supine position. Any of a number of nebulizers may be used in this embodiment. Examples of suitable nebulizers may be found in U.S. Pat. Nos. 5,823,179 and 6,929,003, each entitled "Nebulizer Apparatus and Method", wherein the entirety of each of these patents is hereby incorporated herein by reference.

As has been shown, a patient interface having a central opening in a pacifier-shaped nipple allows for a young patient to receive an aerosolized medicament in a manner that may avoid discomfort or blockage by a tongue. The medicament may originate from a aerosolization catheter connected to a remote supply of medicament and pressurized air, or may be generated with other aerosol generating devices such as metered dose inhalers or nebulizers. When medicament is from an aerosolization catheter, the catheter may be one with one or more lumens and may be positioned inside or just distal to the tip of an interface having a flanged modified pacifier shaped "chamber". In the various embodiments of the pacifier-shaped version of the interface, the typical pacifier tip has been truncated or opened at the distal end creating an open tip conduit. This permits a protected expansion chamber and directional support for an aerosol plume coming off the tip of the multi-lumen tubing. In some embodiments, the pacifier-shaped outer body may include a loose or tightly fitting interface connector that is of a more rigid material than the pacifier-shaped outer body and extends into the insertion portion of the interface to provide extra rigidity or more support for an end of the catheter delivering or generating an aerosol. The aerosol may be directed into the patient's mouth or oral-pharyngeal area, in some embodiments, or may be first directed in to an expansion chamber of holding chamber in other embodiments. The flange of this patient respiratory interface may help position the pacifier body and catheter, and the flange may be positioned outside the mouth or sized to fit just behind the lips in different embodiments. The tip of the catheter or other tubing may also be positioned in an aerosol plume expansion chamber on the proximal side of the flange and pacifier body. A pressure relief or balancing system could be incorporated into or in fluid communication with the chamber created inside the insertion portion to vent or otherwise balance potential excess pressure to the patient created by the catheter's gas flow. Although one example delivery system is noted above, any other type of aerosol delivery or generation system such as a pressurized liquid spray nozzle, dry powder delivery catheter or generator may be incorporated into the insertion portion of the pacifier body version of the patient respiratory interface described above. In alternative embodiments, the insertion portion may also be formed as an extended and curved element that extends downward into the oral-pharyngeal area to direct the aerosol towards the lungs if desired.

It is intended that the foregoing detailed description be understood as an illustration of selected forms that the invention can take and not as a definition of the invention. It is only the following claims, including all equivalents, that are intended to define the scope of the claimed invention. Finally, it should be noted that any aspect of any of the preferred embodiments described herein can be used alone or in combination with one another.

The invention claimed is:

1. A patient respiratory interface comprising:

an insertion portion sized to only extend partially within an oral cavity of a patient;

a flange attached to, and having a surface oriented substantially perpendicular to, the insertion portion, wherein the insertion portion is comprised of a flexible material and is connected to a first side of the flange, and wherein a side of the flange opposite the insertion portion defines a flexible opening;

wherein a supply pathway is defined by the insertion portion and the flange, the supply pathway positioned coaxially along a longitudinal axis of the insertion portion and sized to receive a substance in aerosolized form via the flexible opening;

wherein the insertion portion and flange are arranged in a shape to permit introduction of the substance in aerosol form to an oropharynx of the patient through a center of the insertion portion;

further comprising an expansion chamber having a first opening sized to fit in the flexible opening of the flange and having a second opening for receiving an aerosol in a central region of an interior of the expansion chamber;

wherein a flow path for the substance, defined between the second opening of expansion chamber and the supply pathway of the insertion portion, is unobstructed;

wherein a cross-sectional area of the supply pathway decreases in a direction toward a tip of the insertion portion;

wherein a cross-sectional area of the expansion chamber decreases from the second opening of the expansion chamber to the first opening of the expansion chamber, and an inner surface of the expansion chamber is stepless in the direction of the insertion portion; and wherein the first opening of the expansion chamber and an end of the supply pathway opposite the tip are sized and shaped for a stepless transition from the expansion chamber to the supply pathway.

2. The patient respiratory interface of claim 1, wherein the second opening of the expansion chamber comprises a catheter receiving channel extending into the central region and configured to position a tip of a catheter in the central region.

3. The patient respiratory interface of claim 1, wherein the cross-sectional area of the supply pathway continuously decreases over its length in a direction toward a tip of the insertion portion.

4. A patient respiratory interface comprising:
- an insertion portion sized to only extend partially within an oral cavity of a patient;
- a flange attached to, and having a surface oriented substantially perpendicular to, the insertion portion;
- an expansion chamber having a first opening detachably connected to a flexible opening in a side of the flange opposite the insertion portion, the expansion chamber having a second opening sized to receive and hold at least one lumen, the second opening aligned coaxially with the first opening;
- wherein a supply pathway is defined by the insertion portion, the flange, and the expansion chamber, the supply pathway positioned coaxially along a longitudinal axis of the insertion portion and sized to receive a substance in aerosol form from the at least one lumen;
- wherein the insertion portion and flange are arranged in a shape to permit introduction of the substance in aerosol form to an oropharynx of the patient through a center of the insertion portion;
- wherein a flow path for the substance, defined between the second opening of expansion chamber and the insertion portion, is unobstructed;
- wherein a cross-sectional area of the supply pathway decreases in a direction toward a tip of the insertion portion;
- wherein a cross-sectional area of the expansion chamber decreases from the second opening of the expansion chamber to the first opening of the expansion chamber, and an inner surface of the expansion chamber is stepless in the direction of the insertion portion; and
- wherein the first opening of the expansion chamber and an end of the supply pathway opposite the tip are sized and shaped for a stepless transition from the expansion chamber to the supply pathway.

5. The patient respiratory interface of claim 4, wherein the insertion portion comprises a flexible material defining an opening positioned centrally at a distal end.

6. The patient respiratory interface of claim 4, wherein the substance is aerosolized inside the expansion chamber adjacent the second opening.

7. The patient respiratory interface of claim 4, wherein the substance is carried in the at least one lumen in liquid form.

8. The patient respiratory interface of claim 4, wherein the second opening of the expansion chamber comprises a recessed passageway for receiving the at least one lumen.

9. The patient respiratory interface of claim 8, further comprising a strain relief sleeve positioned within the recessed passageway of the expansion chamber, the strain relief sleeve comprising a hollow cylindrical member having a first end positioned in the recessed passageway and having a second end extending outside the recessed passageway away from the expansion chamber.

10. The patient respiratory interface of claim 4, wherein the first opening of the expansion chamber and a portion of the supply pathway proximate the expansion chamber is sized and shaped substantially the same to avoid obstruction in the flow path.

11. The patient respiratory interface of claim 4, wherein the cross-sectional area of the supply pathway continuously decreases over its length in a direction toward a tip of the insertion portion.

12. A patient respiratory interface comprising:
- an insertion portion sized to only extend partially within an oral cavity of a patient;
- a flange attached to, and having a surface oriented substantially perpendicular to, the insertion portion;
- an expansion chamber removably positioned at one end in the flange and comprising a catheter receiving guide at another end, the catheter receiving guide positioned to hold an end of a catheter inside the expansion chamber;
- wherein a supply pathway is defined by the insertion portion, the flange, and the expansion chamber, the supply pathway positioned coaxially along a longitudinal axis of the insertion portion and sized to receive a substance from the catheter;
- wherein the insertion portion and flange are arranged in a shape to permit introduction of the substance in aerosol form to an oropharynx of the patient through a center of the insertion portion;
- wherein a flow path for the substance, defined between the catheter receiving guide of the expansion chamber and the insertion portion, is unobstructed;
- wherein a cross-sectional area of the supply pathway decreases in a direction toward a tip of the insertion portion;
- wherein a cross-sectional area of the expansion chamber decreases from the second opening of the expansion chamber to the first opening of the expansion chamber, and an inner surface of the expansion chamber is stepless in the direction of the insertion portion; and
- wherein the first opening of the expansion chamber and an end of the supply pathway opposite the tip are sized and shaped for a stepless transition from the expansion chamber to the supply pathway.

13. The patient respiratory interface of claim 12, wherein a diameter of the expansion chamber is greater than a diameter of the insertion portion.

14. The patient respiratory interface of claim 12, wherein an end region of the insertion portion adjacent to a tip comprises an enlarged thickness, such that a diameter of the end region of the insertion portion is greater than a diameter of any other region of the insertion portion.

15. The patient respiratory interface of claim 12, wherein the catheter comprises a multi-lumen tubing configured to generate an aerosol of the substance inside the expansion chamber.

16. The patient respiratory interface of claim 12, wherein an opening of the expansion chamber at the one end of the flange and a portion of the supply pathway proximate the one end is sized and shaped substantially the same to avoid obstruction in the flow path.

17. The patient respiratory interface of claim 12, wherein the cross-sectional area of the supply pathway continuously decreases over its length in a direction toward a tip of the insertion portion.

* * * * *